US005826570A

United States Patent [19]
Goodman et al.

[11] Patent Number: 5,826,570
[45] Date of Patent: *Oct. 27, 1998

[54] DELIVERY OF AEROSOL MEDICATIONS FOR INSPIRATION

[75] Inventors: David E. Goodman, Brookline; Reid M. Rubsamen, Boston, both of Mass.

[73] Assignee: Aradigm Corporation, Hayward, Calif.

[ * ] Notice: The term of this patent shall not extend beyond the expiration date of Pat. No. 5,497,764.

[21] Appl. No.: 847,327

[22] Filed: Apr. 23, 1997

Related U.S. Application Data

[63] Continuation of Ser. No. 457,148, Jun. 1, 1995, abandoned, which is a continuation of Ser. No. 353,162, Dec. 9, 1994, Pat. No. 5,542,410, which is a continuation of Ser. No. 664,758, Mar. 5, 1991, Pat. No. 5,404,871.

[51] Int. Cl.[6] .......... A61M 11/00

[52] U.S. Cl. .......... 128/200.14; 128/200.23; 128/203.12; 128/205.23

[58] Field of Search .......... 128/200.14, 200.16, 128/200.23, 203.12, 204.21, 204.23, 205.23

[56] References Cited

U.S. PATENT DOCUMENTS

| | | | |
|---|---|---|---|
| Re. 29,117 | 1/1977 | Sahajian et al. | 222/70 |
| 3,157,179 | 11/1964 | Paullus et al. | 128/211 |
| 3,187,748 | 6/1965 | Mitchell et al. | 128/173 |

(List continued on next page.)

FOREIGN PATENT DOCUMENTS

| | | |
|---|---|---|
| 028 929 | 5/1981 | European Pat. Off. . |
| 0 045 419 | 2/1982 | European Pat. Off. . |
| 0 136 383 | 4/1985 | European Pat. Off. . |
| 232 235 | 8/1987 | European Pat. Off. . |
| 0 302 958 | 2/1989 | European Pat. Off. . |
| 2 147 177 | 3/1973 | France . |
| 2 437 248 | 4/1980 | France . |

(List continued on next page.)

OTHER PUBLICATIONS

Newman et al., "How Should A Pressurized Beta-Adrenergic Bronchodilator Be Inhaled?", Eur. J. Respir. Dis., 11981) vol. 62, pp. 3–21.

"Aerosol Drug Therapy for the Treatment of Obstructive Airway Disease," pp. 3–16, (Schering Laboratories, Kenilsworth, NJ).

Kohler, "Aerosols for Systemic Treatment", *Lung*, (1990) Suppl: 677–684.

3M HealthCare, Product Information, Jul. 1988, "Aerosol Non-sheathed Actuator and Cap".

Newman et al. "Deposition of Pressurized Aerosols in the Human Respiratory Tract" *Thorax*, 1981 vol. 36, 1981, vol. 35, p. 52.

(List continued on next page.)

*Primary Examiner*—Aaron J. Lewis
*Attorney, Agent, or Firm*—Karl Bozicevic; Bozicevic & Reed LLP

[57] ABSTRACT

Apparatus and methods for delivering an amount of aerosolized medicine for inspiration by a patient in response to the occurrence of appropriate delivery point or points in the patient's detected breath flow. The aerosol medication may be administered as one or more pulses having a pulse width, shape, and frequency that will maximize the respirable fraction of the aerosolized compound being administered. The delivery point or points may be predetermined or determined from a prior inspiratory flow for depositing the selected medication at one or more desired locations in the patient's airway. Determined delivery points are recursively lowered for each inspiratory flow that does not satisfy one of the predetermined and previously lowered threshold. Changes in the patient's breath flow patterns during the course of an aerosolized medication inspiration therapy program may be detected and used to adjust the controlled amount of medication to be delivered in a given administration and/or to inform the patient of the patient's condition or change in condition. The device also may contain a library of administration protocols or operating parameters for different medications and a means for identifying from the canister the medicinal contents of the canister for customizing operation of the apparatus.

11 Claims, 17 Drawing Sheets

U.S. PATENT DOCUMENTS

| | | | |
|---|---|---|---|
| 3,211,346 | 10/1965 | Meshberg | 222/263 |
| 3,356,088 | 12/1967 | Nelson | 128/188 |
| 3,394,851 | 7/1968 | Gorman | 222/402.2 |
| 3,456,644 | 7/1969 | Thiel | 128/173 |
| 3,456,645 | 7/1969 | Brock | 128/173 |
| 3,456,646 | 7/1969 | Phillips et al. | 128/173 |
| 3,464,596 | 9/1969 | Meshberg | 222/402.2 |
| 3,565,070 | 2/1971 | Hanson et al. | 128/173 |
| 3,636,949 | 1/1972 | Kropp | 128/173 R |
| 3,658,059 | 4/1972 | Steil | 128/173 R |
| 3,789,843 | 2/1974 | Armstrong et al. | 128/173 |
| 3,812,854 | 5/1974 | Michaels et al. | 128/200.16 |
| 3,814,297 | 6/1974 | Warren | 222/402.13 |
| 3,826,413 | 7/1974 | Warren | 222/402.13 |
| 3,830,404 | 8/1974 | Frazer | 222/78 |
| 3,878,973 | 4/1975 | Riccio | 222/319 |
| 3,940,023 | 2/1976 | Umstead | 222/153 |
| 3,952,916 | 4/1976 | Phillips | 222/70 |
| 3,968,905 | 7/1976 | Pelton | 222/70 |
| 3,974,941 | 8/1976 | Mettler | 222/70 |
| 3,991,304 | 11/1976 | Hillsman | 235/151.34 |
| 4,106,503 | 8/1978 | Rosenthal et al. | 128/194 |
| 4,117,958 | 10/1978 | Spitzer et al. | 222/402.18 |
| 4,124,149 | 11/1978 | Spitzer et al. | 222/402.19 |
| 4,256,017 | 3/1981 | Eastman | 91/417 R |
| 4,291,688 | 9/1981 | Kistler | 128/200.23 |
| 4,361,401 | 11/1982 | Smith, Jr. et al. | 356/36 |
| 4,366,743 | 1/1983 | Leszczewski | 91/363 R |
| 4,386,553 | 6/1983 | Thoman et al. | 91/361 |
| 4,413,755 | 11/1983 | Brunet | 222/402.2 |
| 4,427,137 | 1/1984 | Dubini | 222/402.2 |
| 4,446,862 | 5/1984 | Baum et al. | 128/203.15 |
| 4,462,398 | 7/1984 | Durkan et al. | 128/200.14 |
| 4,469,255 | 9/1984 | Hill et al. | 222/649 |
| 4,484,577 | 11/1984 | Sackner et al. | 128/203.28 |
| 4,524,769 | 6/1985 | Wetterlin | 128/203.15 |
| 4,534,343 | 8/1985 | Nowacki et al. | 128/200.23 |
| 4,558,710 | 12/1985 | Eichler | 128/720 |
| 4,576,157 | 3/1986 | Raghuprasad | 128/200.23 |
| 4,592,348 | 6/1986 | Waters, IV et al. | 128/200.23 |
| 4,604,847 | 8/1986 | Moulding, Jr. et al. | 53/75 |
| 4,624,251 | 11/1986 | Miller | 128/200.14 |
| 4,648,393 | 3/1987 | Landis et al. | 128/200.23 |
| 4,662,537 | 5/1987 | Wolf et al. | 221/89 |
| 4,664,107 | 5/1987 | Wass | 128/200.23 |
| 4,677,975 | 7/1987 | Edgar et al. | 128/200.14 |
| 4,679,555 | 7/1987 | Sackner | 128/203.15 |
| 4,682,713 | 7/1987 | Clapp | 222/153 |
| 4,693,853 | 9/1987 | Falb et al. | 128/203.14 |
| 4,702,400 | 10/1987 | Corbett | 222/402.2 |
| 4,745,925 | 5/1988 | Dietz | 128/725 |
| 4,790,305 | 12/1988 | Zoltan et al. | 128/200.23 |
| 4,803,978 | 2/1989 | Johnson, IV et al. | 128/200.23 |
| 4,805,609 | 2/1989 | Roberts et al. | 128/200.21 |
| 4,819,629 | 4/1989 | Jonson | 128/203.22 |
| 4,832,012 | 5/1989 | Raabe et al. | 128/200.21 |
| 4,852,582 | 8/1989 | Pell | 128/716 |
| 4,860,740 | 8/1989 | Kirk et al. | 128/203.15 |
| 4,896,832 | 1/1990 | Howlett | 239/322 |
| 4,922,901 | 5/1990 | Brooks et al. | 129/203.26 |
| 4,926,852 | 5/1990 | Zoltan et al. | 128/200.23 |
| 4,932,402 | 6/1990 | Snook et al. | 128/204.23 |
| 4,933,873 | 6/1990 | Kaufman et al. | 364/513.5 |
| 4,934,358 | 6/1990 | Nilsson et al. | 128/200.23 |
| 4,942,544 | 7/1990 | McIntosh et al. | 364/569 |
| 4,984,158 | 1/1991 | Hillsman | 128/725 |
| 5,069,204 | 12/1991 | Smith et al. | 128/200.23 |
| 5,133,343 | 7/1992 | Johnson, IV et al. | 128/200.23 |
| 5,293,865 | 3/1994 | Altner et al. | 128/203.12 |
| 5,497,764 | 3/1996 | Ritson et al. | 128/200.14 |

FOREIGN PATENT DOCUMENTS

| | | | |
|---|---|---|---|
| 2 039 862 | 8/1970 | Germany . | |
| 2 809 255 | 9/1978 | Germany . | |
| 3 617 400 | 11/1987 | Germany . | |
| 3 636 669 | 5/1988 | Germany . | |
| 3 901 963 | 8/1990 | Germany . | |
| 1 377 106 | 2/1988 | U.S.S.R. . | |
| 1 201 918 | 8/1970 | United Kingdom . | |
| 1 270 272 | 4/1972 | United Kingdom . | |
| 1 426 583 | 3/1976 | United Kingdom . | |
| 1 484 010 | 8/1977 | United Kingdom . | |
| 2 004 526 | 4/1979 | United Kingdom . | |
| 2 104 393 | 3/1983 | United Kingdom . | |
| 2 164 569 | 3/1986 | United Kingdom . | |
| 2 186 949 | 8/1987 | United Kingdom . | |
| 2263068 | 7/1993 | United Kingdom | 128/200.23 |
| WO 87/05813 | 10/1987 | WIPO . | |
| 92/07599 | 5/1992 | WIPO . | |
| 9217231 | 10/1992 | WIPO | 128/200.23 |

OTHER PUBLICATIONS

Newman et al. "Deposition of Pressurized Suspension Aerosols Inhaled Through Extension Devices" *Am Rev Respir Dis*, 1981, vol. 124 pp. 317–320.

Moren "Drug Deposition of Pressurized Inhalation Aerosols: II. Influence of Vapor Pressure and Metered Volume", *International Journal of Pharmaceuticals*, 1 (1978) pp. 213–218.

Sullivan et al., "Pneumotachographs: Theory and Clinical Application" *Respiratory Care*, Jul. 1984, vol. 29, No. 7, pp. 736–749.

Bennett, "Targeting Aerosol Delivery in the Lung", *Aerosol Age*, Nov. 1990, pp. 32–35.

3M HealthCare, Product Information, Jul. 1988, "Aerosol System The Standard of Pharmaceutical Precision".

Byron, (ed)., *Respiratory Drug Delivery*, CRC Press, Inc. (1990) pp. 173–178.

Newmann, Deposition and Effects of Inhalation Aerosols, 1983 RAHMS; Lund Tryckeri AB.

McIlreath et al, "The Value of an Automatic Inhalation Device for Asthmatic Children", *The Journal of Asthma Research*, vol. 10, No. 1, Sep. 1972.

Cohen, "'Metered' Aerosols of Bronchodilator Drugs in Clinical Trials", *Thorax* (1971), vol. 2 pp. 316–318.

Spector et al., "Compliance of Patients with Asthma with an Experimental Aerosolized Medication: Implications for Controlled Clinical Trials" *J. Allergy Clin. Immunol.* (1986) vol. 77, pp. 65–70.

Gong, Jr. et al., "Metered–dose Inhaler Usage in Subjects with Asthma: Comparison of Nebulizer Chronolog and Daily Diary Recordings" *J. Allergy Clin. Immunol.* (1988) vol. 82, pp. 5–10.

Cohen, "Color Presentation of Breath Sounds", *Respiration*, vol. 29, pp. 234–246 (1972).

Heyder "Charting Human Thoracic Airways by Aerosols", *Clin. Phys. Physio. Meas.*, 1983, vol. 4, No. 1, pp. 29–37.

Ryan et al. "Standardization of Inhalation Provocation Tests: Two Techniques of Aerosol Generation and Inhalation Compared" *Am. Rev. Respir. Dis.*, (1981), vol. 123, pp. 195–199.

Chai et al., "Standardization of Bronchial Inhalation Challenge Procedures" *J. Allergy Clin. Immunol.*, vol. 56, No. 4, pp. 323–327 Oct. 1975.

Rosenthal et al. "Role of the Parasympathetic System in Antigen–Induced Bronchospasm" *J. Appl. Physiol.: Respirat. Environ. Exercise Phisiol.*, 42(4) pp. 600–606, 1977.

Nieminen et al. "Aerosol Deposition in Automatic Dosimeter Nebulization" *Eur. J. Respir. Dis.*, (1987) 71, pp. 145–152.

Lee et al. "Aerosol Inhalation Teaching Device" *J. Pediatrics.*, 1987, vol. 110, pp. 249–252.

Newman, Stephen P., "Inhalation Apparatus", Deposition and Effects of Inhalation Aerosols, Chapter 2, pp. 23–30 (Lund, Sweden 1983).

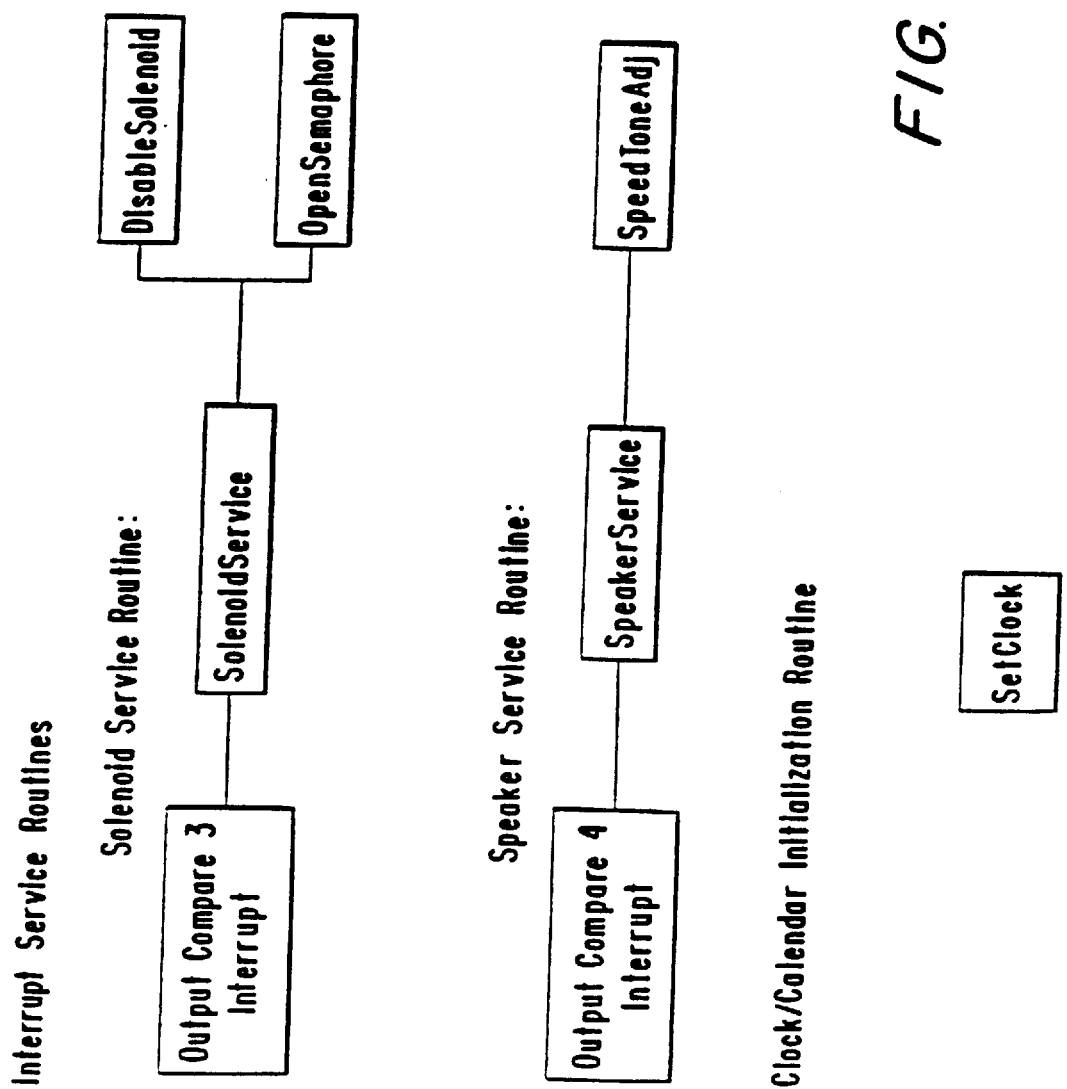

DELIVERY OF AEROSOL MEDICATIONS FOR INSPIRATION

CROSS-REFERENCES TO RELATED APPLICATIONS

This is a continuation of application Ser. No. 08/457,148, filed Jun. 1, 1995, now abandoned, which is a continuation of application Ser. No. 08/353,162, filed Dec. 9, 1994, now U.S. Pat. No. 5,542,410, which is a continuation of application Ser. No. 07/664,758, filed Mar. 5, 1991, now issued as U.S. Pat. No. 5,404,871 to which we claim priority under 35 §120 and which are incorporated herein by reference in their entirety.

This invention relates to delivery of aerosolized materials and specifically to improvements in the delivery of aerosolized medications for inspiration by patients for more effective therapeutic and diagnostic purposes.

BACKGROUND OF THE INVENTION

Devices for the delivery of aerosol medications for inspiration are known. One such device is a metered dose inhaler which delivers the same dosage of medication to the patient upon each actuation of the device. Metered dose inhalers typically include a canister containing a reservoir of medication and propellant under pressure and a fixed volume metered dose chamber. The canister is inserted into a receptacle in a body or base having a mouthpiece or nosepiece for delivering medication to the patient. The patient uses the device by manually pressing the canister into the body to close a filling valve and capture a metered dose of medication inside the chamber and to open a release valve which releases the captured, fixed volume of medication in the dose chamber to the atmosphere as an aerosol mist. Simultaneously, the patient inhales through the mouthpiece to entrain the mist into the airway. The patient then releases the canister so that the release valve closes and the filling valve opens to refill the dose chamber for the next administration of medication. See, for example, U.S. Pat. No. 4,896,832 and a product available from 3M Healthcare known as Aerosol Sheathed Actuator and Cap.

A major problem with metered dose inhalers is that the patient frequently actuates the device at the incorrect time during inspiratory flow to obtain the benefits of the intended drug therapy, e.g., too early or too late in the flow cycle or during expiration.

Another device is the breath actuated metered dose inhaler which operates to provide automatically a metered dose in response to the patient's inspiratory effort. One style of breath actuated device releases a dose when the inspiratory effort moves a mechanical lever to trigger the release valve. Another style releases the dose when the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978.

Existing breath actuated devices have not, however, been entirely successful in overcoming the problem of timing drug delivery to the patient's inspiration. For one thing, breath activated drug delivery is triggered on crossing a fixed threshold inspiratory effort. Thus, an inspiration effort may be sufficient to release a metered dose, but the inspiratory flow following the release may not be sufficient to cause the aerosol medication to pass into the desired portion of the patient's airways. Another problem exists with some patients whose inspiratory effort may not be sufficient to rise above the threshold to trigger the release valve at all.

Other attempts have been made to solve the patient inspiration synchronization problem. U.S. Pat. No. 4,484,577 refers to releasing a dosage of drug into a bag for the patient to inhale and using a bidirectional reed whistle to indicate to the patient the maximum rate of inhalation for desired delivery of the drug or a flow restrictor to prevent the patient from inhaling too rapidly. U.S. Pat. No. 3,991,304 refers to using biofeedback techniques to train the patient to adopt a breathing pattern including tidal volume, respiratory frequency, and inspiration and expiration times for efficient delivery of aerosols for inhalation therapy. U.S. Pat. No. 4,677,975 refers to detecting the beginning of inspiration, and using audible signals and preselected time delays which are gated on the detection of inspiratory flow to indicate to the patient when to inspire and expire, and delivering inhalable material to the mouthpiece a selected time after the detected onset of flow. U.S. Pat. No. 4,932,402 refers to modifying continuous gas flow devices by determining the patient's breathing cycle rate over a period of several breaths and providing pulses of oxygen or other medicinal gases for inhalation during inspiration such that the volume of gas delivered changes in response to changes in the patient's breathing rate. However, these devices also suffer from improper operation by patients who do not conform their breathing to the instructed breathing pattern or whose inspiratory flow does not provide adequate delivery of the medication.

It also is noted that devices exist to deliver dry powdered drugs to the patient's airways as in U.S. Pat. No. 4,527,769 and to deliver an aerosol by heating a solid aerosol precursor material as in U.S. Pat. No. 4,922,901. These devices typically operate to deliver the drug during the early stages of the patient's inspiration by relying on the patient's inspiratory flow to draw the drug out of the reservoir into the airway or to actuate a heating element to vaporize the solid aerosol precursor. However, these devices are subject to improper and variable delivery of the powdered drug or vaporized aerosol, depending on the variations of the patient's inspiration effort and any sustained flow.

A problem with metered dose inhalers is that patients' abilities to use or to be trained to use the device properly vary widely. Thus, whether or not the device is breath actuated, patients may inspire too little medication. Further, in the event that a patient administers an additional dose to compensate for an actual or perceived partial prior dose, too much medication may be inspired. This produces inconsistent and hence inadequate therapy.

Another problem with metered dose inhalers is that they always provide a fixed, uniform dose of medication which is delivered at the time the device is activated. However, in many inhalation therapy programs a gradual reduction in the dose would be more appropriate for the treating the patient's gradually improved condition. In addition, delivery of the dose at different points in the inspiratory flow cycle may be more efficacious than delivery of a single bolus.

It is known that the therapeutic effect of an inhaled drug is affected by where it is deposited in the lungs. The human respiratory tract branches about twenty-three times. The resulting bronchial tree thus contains airway segments having lengths that vary from 12 cm to 0.05 cm, and corresponding diameters that vary from 1.80 cm to 0.041 cm, for an average adult. The smallest airways give rise to the alveoli, the air sacs in contact with the blood stream where gas exchange occurs.

The bronchial tree can be broadly divided into two groups, small airway populations and large airway populations. Specific drugs have different optimal delivery sites within the bronchial tree. For example, bronchodilators used for treating asthma should be deposited in both large and small airways, whereas drugs intended for systemic absorption such as peptides, e.g., insulin, should be deposited as far in the peripheral large airways of the lung as possible.

Studies in Bryon (ed.), *Respiratory Drug Delivery*, CRC Press, Inc. (1990); Newman et al., *Thorax* 1981, 36:52–55; Newman et al. *Thorax*, 1980, 35:234; Newman et al., *Eur. J. Respir. Dis.*, 1981, 62:3–21; and Newman et al., *Am. Rev. Respir. Dis.*, 1981, 124:317–320 indicate that during a single breath of an aerosol compound, only about ten percent of the total aerosol material presented is deposited into the lungs and that the location of deposition in the lung depends upon 1) breath parameters such as volume of inspiration, inspiratory flow rate, inspiratory pause prior to expiration, the lung volume at the time the bolus of medication is administered, and expiratory flow rate, 2) the size, shape and density of the aerosol particles (i.e., the medicinal compound, any carrier, and propellant), and 3) the physiological characteristics of the patient.

Bryon reports that if the deposition fraction is plotted as a function of the airway generation number (See Table I), a bimodal distribution is obtained as illustrated in FIG. 1. The first peak is produced because inertial impact is maximal in the larger airways where airways velocity is highest. This effect is not seen in medium sized airways where velocity is lower and airway size is too large to permit deposition by sedimentation under gravity. The second peak appears in the more distal and smaller airways where velocity is slowest and deposition by sedimentation occurs.

TABLE I

Airway Lengths and Diameters from the Morphological Model of Weibel (Bryon, Respiratory Drug Delivery, CRC Press (1990))

| Generation | Length (cm) | Diameter (cm) |
|---|---|---|
| 0 | 12.000 | 1.800 |
| 1 | 4.760 | 1.220 |
| 2 | 1.900 | 0.830 |
| 3 | 0.760 | 0.560 |
| 4 | 1.270 | 0.450 |
| 5 | 1.070 | 0.350 |
| 6 | 0.900 | 0.280 |
| 7 | 0.760 | 0.230 |
| 8 | 0.640 | 0.186 |
| 9 | 0.540 | 0.154 |
| 10 | 0.460 | 0.130 |
| 11 | 0.390 | 0.109 |
| 12 | 0.330 | 0.095 |
| 13 | 0.270 | 0.082 |
| 14 | 0.230 | 0.074 |
| 15 | 0.200 | 0.066 |
| 16 | 1.165 | 0.060 |
| 17 | 0.141 | 0.054 |
| 18 | 0.117 | 0.050 |
| 19 | 0.099 | 0.047 |
| 20 | 0.083 | 0.045 |
| 21 | 0.070 | 0.043 |
| 22 | 0.059 | 0.041 |
| 23 | 0.050 | 0.041 |

The Bryon and Newman studies also suggest that the modal distribution pattern, and thus the relative location of deposited medication, can be modified by changing those parameters.

The Newman references refer to measuring inspired air with a pneumotachograph to obtain a flow rate signal, which is integrated by a computer to determine lung capacity. A determined lung capacity, as a percent of vital capacity, is used as a threshold to actuate a solenoid to depress the canister of a metered dose inhaler on the inspiration of the predetermined lung volume.

A problem with existing metered dose inhalers, whether or not breath actuated, is that they are factory preset for a given particle size distribution and that distribution cannot be varied. Thus, those devices are not capable of selecting a maximum desired respirable fraction of the aerosol mist that is suitable for a desired location of delivery of the medication. Further, metered dose devices, and in particular breath actuated devices, cannot deliver a metered dose having a selectable respirable fraction in response to an identified point in the patient's inspiratory flow to provide for selective deposition of the medication in selected areas of the lungs.

Devices for controlling particle size of an aerosol are known. U.S. Pat. No. 4,790,305 refers to controlling the particle size of a metered dose of aerosol for delivery to the walls of small bronchi and bronchioles by using a first container into which the medication is delivered prior to inspiration by the patient and a second collapsible container which contains a fixed volume of air to be inspired immediately prior to inspiration of the metered dose of medication, and flow control orifices to control the flow rate. U.S. Pat. No. 4,926,852 refers to metering a dose of medication into a flow-through chamber that has orifices to limit the flow rate to control particle size. U.S. Pat. No. 4,677,975 refers to a nebulizer device that uses baffles to remove from an aerosol particles above a selected size which particles may be returned to the nebulizer for reuse. U.S. Pat. No. 3,658,059 refers to a baffle that changes the size of an aperture in the passage of the suspension being inhaled to select the quantity and size of suspended particles delivered. A problem with these devices is that they process the aerosol after it is generated and thus are inefficient and wasteful.

It is well known that pulmonary functions, such as forced expiratory volume in one second, forced vital capacity, and peak expiratory flow rate, can be measured based on measured flow rates and used both to diagnose the existence of medical conditions, and to ascertain the efficacy of a drug therapy program. See for example, U.S. Pat. Nos. 3,991,304 and 4,852,582 and the Newman references discussed above. Heretofore, these tests have been performed using available spirometers. U.S. Pat. No. 4,852,582 also refers to using a peak flow rate meter to measure changes in peak flow rate before and after administration of a bronchodilator. The results of such tests before and after administration of several different medications are used to evaluate the efficacy of the medications, which are then used and compared to various laboratory standard or predetermined data to make a diagnosis and prescription for treatment of the patient's condition.

A problem with the foregoing pulmonary function test devices is that they are complicated for most patients to perform. Another problem is that the test data must be examined and interpreted by a trained medical practitioner to be meaningful. Another problem is that they do not provide adequately for altering the dosage of the medication administered in a single patient during the course of therapy, or from patient to patient, using the same delivery device for generating an aerosol of the same or different medications.

SUMMARY OF THE INVENTION

It is, therefore, an object of this invention to provide improved apparatus, systems, and methods for delivering aerosol compounds for inspiration by a patient.

It is another object of this invention to provide improved apparatus, systems, and methods for delivering for inspiration an aerosol having a particle size distribution favorable for selective deposition into desired locations in a patient's pulmonary system. It is another object to release a controlled amount of aerosol in one or more pulses having a selected pulse size, shape, and frequency and number of pulses to produce a selected particle size distribution. It is another object to provide a variably actuated valve mechanism having an open state and a closed state for controlling the medication pulse size, shape, and frequency, to produce a pulse train having a selected particle size distribution at a selected point or a series of selected points in the patient's inspiratory flow and, further, to produce a pulse train so that the particle size distribution delivered at different points in the flow may be different.

It is another object of the invention to deliver aerosolized compounds in response to a measure of a patient's breathing pattern during inspiration. It is another object to select the optimal point or points for release of one or more pulses of medication based on an analysis of the patient's inspiratory flow in a first detected flow and to release the medication on the occurrence of the determined point or points during a subsequently detected inspiratory breath.

It is another object to select the location of deposition of the medication in the patient's airway by selecting the optimal point or points in the inspiratory flow to achieve such deposition. It is another object to deposit selectively the medication based on a selected optimal flow point and a selected pulse train to obtain a desired respirable fraction for such deposition. It is another object to prompt the patient to hold his or her breath for an optimal period of time at the end of inspiration to optimize delivery of the aerosolized compound being administered.

It is another object of the invention to release automatically a controlled amount of medication when the patient's detected inspiratory flow exceeds a preselected or default delivery threshold, and, if the first detected flow does not exceed (or satisfy) the default delivery threshold, to determine a new delivery threshold based on a detected flow maxima parameter of the previously detected inspiratory flow not exceeding the prior delivery threshold and to release a controlled amount of medication when a subsequently detected flow exceeds the new determined delivery threshold. The determined threshold is thus recursively determined for each detected inspiratory flow not exceeding the previously established delivery threshold, whether that threshold is the preselected default triggering threshold or a subsequently determined threshold.

It is another object of this invention to provide improved apparatus, systems, and methods for delivering aerosolized compounds for inspiration by a patient by incorporating a measure of a patient's pulmonary function to provide for varying the dosage or controlled amount of the aerosolized compound delivered for inspiration by the patient in response to detected changes in the patient's pulmonary function during a course of therapy directed to improving pulmonary function.

It is another object to provide improved apparatus, systems, and methods for delivering aerosol compounds for inspiration by a patient by incorporating a measure of a patient's pulmonary function and an acuity display of that function to the patient, for example, to provide for alerting the patient whether the patient's determined function indicates whether the patient should continue the inhalation drug therapy program or seek immediate medical attention.

It is another object of the present invention to provide a programmable, durable variable dose inhaler whereby the medication being administered can be selected and the inhaler can be programmed to provide for efficacious delivery of the selected medication to a given patient. It is another object to provide such a device with a library of information regarding medications to be administered and their respective administration protocols. It is another object to provide an improved inhaler with audible, visual or audiovisual feedback for prompting the patient to obtain a suitable breathing pattern for delivering a selected medication at an appropriate time based on the patient's detected inspiratory flow and, optionally, for measuring a pulmonary function. It is another object to provide feedback for prompting the patient's breathing pattern in response to previously measured pulmonary or flow parameters for automatic administration of the selected medication. It is another object to provide a visual display of the adequacy of a dosage delivered and other parameters regarding the course of therapy, such as time of next dose to be administered. It is another object to provide the medical examiner with a history log of drug administration and points of drug delivery for evaluation.

A further object of the present invention is to provide a hand held microprocessor controlled inhaler device for use in outpatient aerosol drug therapy that is capable of autonomously modifying the initial therapy program based on detected progressive changes in the patient's breath flow and corresponding pulmonary functions. It is another object to provide for communications between the device and a remote station for remote reprogramming of the microprocessor controlled device for external modification of the therapy or for transmitting historical log data for evaluation.

It is another object to provide a disposable mouthpiece containing a nozzle for dispensing medication and a flow rate sensor located in the flow path to detect flow so that it does not interfere with generation of an aerosol for inspiration by a patient.

The present invention increases the effectiveness and utility of devices for delivering aerosolized medications and overcomes the problems of the prior known devices. Broadly, the invention concerns methods and apparatus for achieving the above objectives based on detecting the patient's inspiratory flow and releasing one or more pulses of an aerosol medication respectively at one or more identified points in the detected flow to provide an efficacious delivery of a selected amount of medication.

The following terms are used in describing the present invention. The term "delivery point" refers to a point in the detected inspiratory flow at which an amount of aerosol is to be delivered. The term "amount of aerosol" refers to the amount released in response to the occurrence of a delivery point and may be either a single pulse, or a preselected number of pulses, e.g., four pulses having the same shape and frequency. The term "delivery schedule" refers to one or more delivery points in the detected inspiratory flow such that a full dosage of aerosol is delivered in accordance with the delivery schedule. Thus, a delivery schedule that includes only one delivery point will deliver an amount of aerosol in response to the occurrence of that point in the detected inspiratory flow that corresponds to a full dosage, and a delivery schedule that includes more than one delivery point will deliver an amount of aerosol in response to the occurrence of each point in the delivery schedule in the detected inspiratory flow such that the sum of the amounts total the full dosage. The term "delivery threshold" refers to the first delivery point in the delivery schedule such that if a detected inspiratory flow satisfies the delivery threshold, the event is considered to be a successful delivery of aerosol, notwithstanding that for delivery schedules having more than one delivery point, subsequent delivery points in the delivery schedule may not be satisfied such that a full dosage is not delivered. The term "flow" refers to one of a flow rate in volume per time, a flow volume (which may be calculated from the time integral of the determined flow rate), and a combination of flow rate and flow volume.

One aspect of the invention concerns an oral drug delivery device that delivers each dosage as a sequence of pulses selected to increase the effective respirable fraction of medication delivered compared to a conventional metered dose inhaler device. More particularly, each pulse is provided with a selected pulse width, shape, and frequency that will maximize the respirable fraction of the aerosolized compound being delivered. This pulse selection also will allow manipulation of the cumulative particle size distribution so as to enhance delivery of the aerosolized compound to desired loci in the airway.

One preferred embodiment of this aspect of the invention is directed toward an apparatus for controlling the particle size distribution to maximize the respirable fraction of an aerosol. One such device includes:

(a) a source of aerosol generating material;

(b) a valve, associated with the source, having a first state for releasing an amount of aerosol generating material and a second state for not releasing an amount of aerosol generating material;

(c) means for selecting the relative time the valve is in the first state and the second state to maximize respirable fraction of an aerosol pulse, the valve being in the first state for a time selected from between about 10 to about 1000 msecs; and (d) means for cycling the valve between states in response to the selected relative time to release an amount of aerosol having the maximized respirable fraction, wherein the valve is cycled at a rate at or below 100 cycles per second.

Another preferred embodiment of this aspect of the invention concerns a method for controlling the respirable fraction of an aerosol in an aerosol drug delivery device having a source of aerosol generating material and a valve having a first state for releasing an amount of aerosol generating material and a second state for not releasing an amount of aerosol generating material. One such method includes:

(a) selecting the relative time the valve is in the first state and the second state to select the maximum respirable fraction of an aerosol pulse, the valve being in the first state for a time selected from between about 10 to about 1000 msecs; and (b) cycling the valve from the second state to the first state to the second state in response to the selected relative time to release an amount of aerosol having the maximized respirable fraction, the cycling occurring at a rate at or below 100 cycles per second.

In varying embodiments of the apparatus or method, the valve may be opened in the first state for a time in the range of from 10 to about 1000 msecs, otherwise being in the second state for the duration of the cycle, to produce a mist having a cumulative particle size distribution selectively favoring small or large particles. The relative time the valve is in the first state and the second state may be selected so that the valve is operated asynchronously or synchronously to produce one or more pulses such that each full dosage of aerosol includes one pulse or more than one pulse of non-uniform or uniform pulse widths, shapes, and intervals between pulses. Preferably, the valve is cycled in response to a detected inspiratory flow satisfying a provided delivery schedule. Further, the pulses may be provided with selected particle size distributions that vary from pulse to pulse whether in response to the same or different delivery points.

In a preferred embodiment, the valve and the operating valve means are an electromechanically controlled valve actuator, such as an integral solenoid and valve, for metering the contents of a pressurized canister to provide an aerosol pulse train having, for example, synchronous pulses of uniform size, asynchronous pulses of uniform size, synchronous pulses of non-uniform size, asynchronous pulses of non-uniform size, and combinations thereof. The integral solenoid and valve device is preferably interposed in a flow channel from the source of aerosol generating material to a nozzle that produces the aerosol. Preferably, a series of four pulses having a duty cycle of from 8 to 15% are used to deliver an amount of aerosol in response to each delivery point in a delivery schedule satisfied by the flow. Thus, the delivery schedule provided may be selected so that the given respirable fraction of the one or more pulses will be deposited in a desired location in the patient's airways. In this regard, particles intended for deep airway deposition would be delivered in the inspiratory flow earlier, or at lower flow rates and volumes, than particles intended for deposition in peripheral airways.

Another aspect of the present invention concerns an apparatus for selecting the delivery schedule based on the patient's measured inspiratory flow.

In a preferred embodiment, the apparatus has a preprogrammed, default delivery schedule whereby if the patient's first detected inspiratory flow does not satisfy the first delivery point, namely, the delivery threshold, for the default delivery schedule, the apparatus enters a calibration mode. The delivery schedule is further selected for depositing the particles in the desired location for efficacious treatment of the patient. In this embodiment, the term "first detected inspiratory flow" refers to the first inspiratory flow detected subsequent to a selected event, i.e., a reset flow event, for example, the apparatus being turned on, the device being reset, a successful delivery of an aerosol, and the expiration of a selected time interval without delivery of an areosol.

In the calibration mode, the apparatus selects a new delivery schedule of one or more points based on the preceding inspiratory flow (which failed to satisfy its delivery threshold), prompts the patient to take another breath, and, on satisfaction of the newly selected delivery threshold during the subsequently detected inspiratory flow, delivers the aerosol in accordance with the delivery schedule to the extent that any subsequent delivery points are satisfied by the detected inspiratory flow. Thus, the patient receives the selected aerosol medication at the determined optimal delivery point or points for depositing the administered aerosolized compound at preferred loci in the lung.

Once in the calibration mode, if a subsequent breath does not satisfy the newly determined delivery threshold, a recursive routine is used for selecting a new delivery threshold for each successive inspiratory effort that does not satisfy a delivery point threshold which results in successively lowering the delivery threshold by a predetermined amount. The predetermined amount is preferably a sequence of predetermined percentages of the measured flow of the preceding inadequate breath. For delivery schedules having more than one delivery point, typically all delivery points will be lowered by the same percentage as the threshold point. Thus, the device is configured to deliver eventually medication to the patient taking into consideration the patient's inspiratory abilities at the time of dosage administration and the aerosol medication to be delivered. The delivery threshold may be based on an inspiratory flow rate, more particularly, a selected rate prior to the occurrence of the peak inspiratory flow rate, e.g., for a preselected threshold a rate in the range of 20 to 30 liters per minute, an inspiratory flow volume e.g., for a preselected threshold a volume of about 1.0 liter, or, more preferably, a combination of a flow rate and a flow volume. Preferably, once a delivery of aerosol is made, the apparatus will return to its preprogrammed default operating mode and preselected delivery schedule whether or not the full dosage of aerosol has been administered.

One preferred embodiment of this aspect of the invention is directed towards an apparatus for delivering an aerosol from a supply of aerosol generating material for inspiration by a person in response to the detected inspiratory flow of the person. One such apparatus includes:

a valve in communication with the supply of aerosol generating material;

means for operating the valve to release an amount of aerosol generating material to form an aerosol;

means for detecting an inspiratory flow of the person;

means for controlling the valve operating means in response to the detected inspiratory flow comprising:

first means for determining whether each detected inspiratory flow is one of a first flow or a subsequent flow, the first flow corresponding to one of the first attempt to deliver an amount of aerosol and the first attempt to deliver an amount of aerosol following delivery of an amount of aerosol, the subsequent flow corresponding to an inspiratory flow detected subsequent to a preceding detected inspiratory flow not followed by delivery of an amount of aerosol;

means for providing a delivery threshold corresponding to a point in the detected inspiratory flow at which an amount of aerosol is to be delivered, the provided delivery threshold being a preselected delivery threshold in response to the detected inspiratory flow being determined to be a first flow, and a determined delivery threshold in response to the detected inspiratory flow being determined to be a subsequent flow, the providing means including means for calculating the determined delivery threshold based on the preceding detected inspiratory flow; and second means for determining whether or not the detected inspiratory flow satisfies the provided delivery threshold so that the controlling means operates the valve to deliver an amount of aerosol in response to the second determining means determining that the detected inspiratory flow satisfies the provided delivery threshold.

Another aspect of this embodiment of the invention is directed toward a method of delivering an aerosol to a person for inspiration using a device having a supply of aerosol generating material and a valve for releasing an amount of aerosol generating material to form an aerosol, and a means for detecting inspiratory flow of the person. One such method includes the steps of:

(a) detecting an inspiratory flow of the person;

(b) determining whether each detected inspiratory flow is one of a first flow or a subsequent flow, the first flow corresponding to one of the first attempt to deliver an amount of aerosol and the first attempt to deliver an amount of aerosol following delivery of an amount of aerosol, the subsequent flow corresponding to an inspiratory flow detected subsequent to a preceding detected inspiratory flow not followed by delivery of an amount of aerosol;

(c) selecting a delivery threshold corresponding to a point in the detected inspiratory flow at which an amount of aerosol is to be delivered so that a preselected delivery threshold is selected in response to determining that the detected inspiratory flow is a first flow, and a determined delivery threshold is selected in response to determining that the detected inspiratory flow is a subsequent flow; and (d) determining whether or not the detected inspiratory flow satisfies the selected delivery threshold; and (i) in response to the detected inspiratory flow satisfying the selected delivery threshold, operating the valve to release an amount of aerosol generating material to form an aerosol; or (ii) in response to determining that the detected inspiratory flow did not satisfy the selected delivery threshold, calculating a new delivery threshold based on the detected inspiratory flow so that the selected delivery threshold for the next detected inspiratory flow determined to be a subsequent flow is the calculated delivery threshold.

In a preferred embodiment of this aspect of the invention, the calculating means and method step for providing the determined delivery threshold determines the delivery threshold based on the detection of an inspiratory flow not satisfying the provided delivery threshold, and can recursively determine new delivery thresholds for each successive detected inspiratory flow that fails to satisfy each provided delivery threshold, notwithstanding that the delivery thresholds are successively lowered. One such calculating means includes:

means for measuring a selected flow parameter of the detected inspiratory flow in response to second determining means determining that the detected inspiratory flow did not satisfy the provided delivery threshold; and means for adjusting the provided delivery threshold in response to the measured flow parameter, thereby providing the determined delivery threshold.

One method includes measuring a selected flow parameter of the detected inspiratory flow in response to determining that the detected inspiratory flow did not satisfy the selected delivery threshold and adjusting the selected delivery threshold in response to the measured flow parameter. The selected flow parameter may be a point corresponding to the detected maxima of flow rate, flow volume, or some combination of flow rate and flow volume, such that the adjustment is a percentage of the detected flow parameter.

Preferably, the delivery threshold further comprises a delivery schedule including the delivery threshold as the first delivery point and one or more additional delivery points in the detected flow following the delivery threshold, such that an amount of aerosol is to be delivered at each delivery point in the schedule. Also, for detected inspiratory flows that are determined to be subsequent flows, adjusting the delivery schedule adjusts every point in the delivery schedule and determining whether or not the detected inspiratory flow satisfies the delivery threshold also determines whether or not each delivery point in the delivery schedule is satisfied so that an amount of aerosol is delivered for each delivery point in the delivery schedule that is satisfied by the detected inspiratory flow.

In an alternate embodiment of this aspect of the invention, concerning selecting the delivery schedule based on the person's measured inspiratory flow, the apparatus is configured to operate in a mode whereby a first inspiratory flow is detected, a delivery schedule corresponding to the optimal delivery threshold (and optionally additional delivery points) for the administration of the selected aerosol medication is determined based on a measure of the detected inspiratory flow parameters, and a subsequently detected inspiratory flow is detected and compared to the delivery schedule whereby an amount of aerosol will be delivered in accordance with the delivery schedule upon satisfaction of each delivery point in the determined delivery schedule by the subsequently detected inspiratory flow.

One such apparatus includes:

(a) a reservoir containing an aerosol generating material;

(b) valve means for releasing an amount of the aerosol generating material from the reservoir, thereby to form an aerosol;

(c) means for detecting an inspiratory flow of the person including a first inspiratory flow and a second inspiratory flow occurring subsequent to the first inspiratory flow;

(d) first means for evaluating the first detected inspiratory flow to identify an appropriate delivery threshold for the delivery of an aerosol;

(e) second means for evaluating the second detected inspiratory flow and determining whether the second detected flow satisfies the determined delivery threshold; and (f) means for actuating the valve means in response to the second detected inspiratory flow satisfying the delivery threshold, thereby to deliver an amount of aerosol during the second detected inspiratory flow.

Another aspect of this alternate embodiment of the invention is directed to a method of administering a controlled amount of medication using a device having a supply of aerosol generating material and a valve for releasing an amount of aerosol generating material to form an aerosol and a means for detecting an inspiratory flow of a person. One such method includes the steps of:

(a) detecting a first inspiratory flow of the person;

(b) determining a delivery threshold for the delivery of an amount of aerosol based on the first detected inspiratory flow;

(c) detecting a second inspiratory flow of the person;

(d) determining whether or not the detected second inspiratory flow satisfies the determined delivery threshold; and (e) operating the valve to deliver the amount of aerosol in response to determining that the second inspiratory flow satisfies the determined delivery threshold.

Preferably, in the apparatus and methods of this alternate embodiment, for each second inspiratory flow that does not satisfy a determined delivery threshold, the second inspiratory flow is treated as the first inspiratory flow such that the first determining means determines a new delivery threshold based on the evaluation of that detected inspiratory flow. Another inspiratory flow is then detected (the third) and treated as the second detected inspiratory flow. Thus, the second determining means evaluates the latter flow and determines whether it satisfies the determined delivery threshold based on the preceding flow. The apparatus will continue to determine a new delivery threshold based on a selected detected inspiratory flow, which threshold is used for a following detected inspiratory flow. In this manner, the apparatus will eventually deliver an amount of aerosol medication to the person, even in the event of a degrading inspiratory flow effort. In other respects, this alternate embodiment is similar in operation to the previously described embodiment.

In either embodiment the dosage of aerosol medication may be adjusted over time based on measured changes in the patient's pulmonary functions and, further, each dosage is released based on a delivery schedule, either determined, preprogrammed or recursively determined, so that the administration of aerosol medication occurs automatically in accordance with a desirable delivery schedule in the patient's detected inspiratory flow and with a particle size distribution to maximize the efficacy of the medication.

In either embodiment of this aspect of the invention, the means for detecting the inspiratory flow is preferably a tube defining an inspiratory flow path having a mouth end and an open end and a flow transducer disposed in the flow path. The flow transducer may be selected from among a flow resistive device which generates a pressure drop across the device (referred to as a differential pressure transducer) and an associated means for converting the measured differential pressure into an inspiratory flow rate, e.g., a pneumotach, a hot wire anemometer and means for converting the measured temperature changes into an inspiratory flow rate, and similar devices for providing a flow rate signal. Preferably, the inspiratory flow path includes a means for providing a laminar flow through the inspiratory flow path so that the flow transducer detects the differential pressure across a laminar air flow. The laminar flow provides a flow and a flow path having linear characteristics for converting the differential pressures to flow rate. In embodiments not having a laminar flow means or using transducers and/or inspiratory flow paths not having such linear flow characteristics, such as venturi ports or a single resistive flow screen, the flow path may be encoded by an array of predetermined calibration constants such that nonlinear characteristics of the differential pressures detected across the flow resistive device may be converted by use of the calibration constant array for the range of pressures detected to flow rates, directly or indirectly. Preferably, a differential pressure transducer for use in the present invention will have a differential pressure sensitivity in the range of ±25.4 cm of water corresponding to a flow rate of from about 0 to about 800 liters per minute.

Another aspect of the invention concerns methods and apparatus for monitoring the patient's breath flow patterns during the course of an aerosolized medication inspiration therapy program and determining the patient's pulmonary function based on detected flow. In one embodiment, a display device is provided for displaying the patient's determined pulmonary function. The display device may be used to indicate the patient's instantaneous condition when an instantaneous pulmonary function is measured, to indicate relative changes in condition when a subsequent measure of the pulmonary function is compared to a prior measure or historical average of the measures (e.g. a weighted average) of that pulmonary function, or both. Importantly, this display will indicate to the patient when measured functions indicate that the patient should seek medical attention. Thus, the present invention is believed to overcome the problem of patients not knowing whether their medical condition is better, worse or unchanged, or is being adequately treated during the course of medication.

In another embodiment, the relative changes in measured pulmonary function, whether the change is determined from one administration of medication to the next, or from a baseline measured pulmonary function (or a weighted average historical record) to the next administration of medication, in addition to displaying the condition, also may be used to adjust the dosage of medication based on the determined changes in the determined function. Thus, this aspect of the present invention provides for optimizing the effectiveness of the medication within the limits of preselected parameters, considering such things as maximum allowable dosages for the given patient and the frequency of medication.

One embodiment of this aspect of the invention is directed towards an apparatus and method for measuring the patient's pulmonary function and displaying a visual acuity of the measured function to the patient. One such apparatus includes means for detecting a breath parameter of the person selected from among one or more of inspiratory flow and expiratory flow;

means for determining a pulmonary function of the person based on a measure of at least one of the detected breath parameters;

a first visual indicator corresponding to a first range of pulmonary conditions for the determined pulmonary function; and a second visual indicator corresponding to a second range of pulmonary conditions for the determined pulmonary function, the first and second ranges being contiguous;

means for evaluating the determined pulmonary function and illuminating the one of the first and second visual indicators whose corresponding range includes the determined pulmonary function.

More than one visual indicator may be used, more preferably three visual indicators corresponding to three contiguous ranges of conditions, respectively, nominal condition, marginal condition, and unacceptable condition.

In a preferred embodiment, the apparatus of this aspect of the invention may be configured to acquire a second measure of pulmonary function, compare that measure to a prior measure, and display trend data to the patient, thereby to indicate whether the person's medical condition is improving, degrading, or remaining about the same. One such apparatus includes:

means for comparing a first determined pulmonary function to a second determined pulmonary function and indicating whether or not the patient's determined pulmonary function has changed from the first to the second determinations, the first determined pulmonary function being based on a first detected breath parameter and the second determined pulmonary function being based on a second detected breath parameter subsequent to the first detected breath parameter; and means for displaying whether the detected pulmonary function has improved on a first visual indicator, remained nominally the same on a second visual indicator, and degenerated on a third visual indicator in response to the indicated change in the first and second determined pulmonary functions.

One method of this aspect of the invention includes the steps of:

(a) detecting a breath parameter of the person selected from among one or more of an inspiratory flow and an expiratory flow;

(b) determining a pulmonary function of the person based on a measure of at least one of the detected breath parameters;

(c) selecting a first range of pulmonary conditions for the determined pulmonary function and a second range of pulmonary conditions for the determined pulmonary functions, the first and second ranges being contiguous;

(d) providing a first visual indicator corresponding to the first selected-range and providing a second visual indicator corresponding to the second selected range;

(e) evaluating the determined pulmonary function with respect to the first and second selected ranges and identifying which range includes the determined pulmonary function; and (f) illuminating the visual indicator corresponding to the identified selected range including the determined pulmonary function.

Preferably, the method includes providing more than two contiguous ranges of pulmonary conditions and more than two corresponding visual indicators for each selected range so that, for example, the measured pulmonary function can be compared to ranges of nominal, marginal, and unacceptable ranges of pulmonary conditions, and the visual indicator corresponding to the selected range including measured pulmonary function can be illuminated.

In an alternate embodiment of the above method, the method includes acquiring a second breath parameter subsequent to the previously measured pulmonary function and measuring a second pulmonary function, comparing the second measured pulmonary function to the first measured pulmonary function, indicating whether or not the patient's determined pulmonary function has changed from the first to the second determinations, providing a first, second, and third visual indicators, and displaying whether the second measured pulmonary function has improved on the first visual indicator, remained nominally the same on the second visual indicator, and degenerated on the third visual indicator, relative to the previously measured pulmonary function.

Another preferred embodiment of this aspect of the invention is directed to an apparatus for selecting the dose of aerosol medication for inspiration by a patient in response to detected changes in pulmonary function. One such apparatus comprises:

(a) a reservoir containing an aerosol generating material including medication;

(b) means for detecting a patient's breath flow;

(c) means for calculating a pulmonary function in response to a detected breath flow;

(d) means for determining a first pulmonary function in response to a first detected breath flow;

(e) means for determining a second pulmonary function corresponding to a second detected breath flow, the second detected breath flow occurring subsequent to the first detected breath flow;

(f) means for comparing the first determined pulmonary function and the second determined pulmonary function to identify relative changes in pulmonary function over time; and (g) means for releasing a controlled amount of medication from the reservoir in response to the first and second determined pulmonary functions so that the controlled amount is adjusted for identified relative changes in the first and second determined pulmonary functions.

Preferably, the apparatus and methods further provide means for identifying the appropriate delivery schedule in a detected inspiratory flow for releasing the dosage of aerosol medication, and means for delivering a dosage of aerosol adjusted in response to identified relative changes in the first and second pulmonary functions, a subsequently detected inspiratory flow satisfying the delivery schedule. Means for recursively adjusting the delivery schedule may be provided when a detected inspiratory flow does not satisfy a delivery threshold.

This aspect of the invention also is directed to a method for adjusting the controlled amount of medication in response to detected changes in pulmonary function over time. One such method includes the steps of:

(a) detecting a patient's first breath flow;

(b) determining a first pulmonary function in response to the detected first breath flow;

(c) detecting a patient's second breath flow subsequent to the first breath flow;

(e) determining a second pulmonary function in response to the detected second breath flow;

(f) comparing the first and second determined pulmonary functions and identifying relative changes between the first and second determined pulmonary functions; and (g) adjusting the amount of aerosol to be delivered in response to the identified changes in pulmonary function.

It should be understood that, in the context of comparing two measured pulmonary functions, the term first breath flow or first detected pulmonary function may be one of the previously acquired measurement, a baseline measurement made at the beginning of the medication therapy, and a changing weighted average of previously acquired measurements, whereby the weights may be selected to favor more recently acquired or less recently acquired measurements. Thus, the latter acquired measurement may be compared to such a first measurement for indicating short term relative changes, absolute changes from a baseline, or more long term relative changes.

Another aspect of the invention concerns providing the device with a memory for containing a library of administration protocols or parameters for different medications and their applications and a means for identifying the medicinal contents of the canister, and optionally, the application for such medication. Preferably, the canister is provided with h code identifying the medication, and the device receptacle for the canister includes means for reading the canister code when the canister is inserted in the receptacle. The information is then used for reprogramming the device for delivering the medication identified, for example, during a power-up or reset operation. Suitable canister codes include product labeling such as a bar code, a factory set resistor value, or a read only memory device, e.g., a byte of digital data, such that the means for reading the code can read the bar code, resistor value or memory byte contents, which information is then used to identify the medication by, for example, reference to a look-up table or preprogrammed software control subroutines.

One embodiment of this aspect of the invention is directed toward a system for releasing an aerosol for inspiration by a patient comprising:

(a) a reservoir of a selected medication;

(b) means for identifying the selected medication, said means being associated with the reservoir;

(c) valve means for releasing the selected medication from the reservoir, thereby to form an aerosol;

(d) means for actuating the valve means to deliver a controlled amount of the selected medication as an aerosol; and (e) means for controlling the actuating means comprising:

(i) means responsive to the identifying means for obtaining the identity of the selected medication, and (ii) means for containing the operating parameters for administering a controlled amount of the selected medication, whereby the controlling means controls the actuating means to release a controlled amount of the selected medication in accordance with the operating parameters associated with the identified selected medication.

In one preferred embodiment the containing means includes a library containing the operating parameters for each of a plurality of medications so that identification of the selected medication in the reservoir provides for the controlling means, preferably a microprocessor device, selecting from the library the operating parameters corresponding to the identified selected medication for use in controlling the release of the selected medication for inspiration by the patient. In an alternate embodiment, the apparatus also includes a means for receiving operating parameters for identified medications not within the containing means, whether or not the containing means includes a library of medications, and for providing the received operating parameters to the controlling means. Such input may be provided externally by a medical practitioner or by memory contained in a read only memory device associated with the canister.

Another embodiment of this aspect of the invention is directed towards a method for releasing an aerosol for inspiration by a patient in a device including a reservoir of aerosol generating material including a medication, a valve for releasing medication from the reservoir, and a means for controlling the valve for delivering an amount of the aerosol medication for inspiration by the patient. One such method includes the steps of:

(a) providing the reservoir with an associated code corresponding to the medication in the reservoir;

(b) providing the controlling means with the operating parameters for releasing a dosage of the medication;

(c) identifying the code associated with the reservoir;

(d) selecting the operating parameters for the medication of the identified codes from the operating means; and (e) operating the valve to deliver the dosage of aerosol medication in accordance with the selected operating parameters for the medication.

In a preferred embodiment, the method step (b) includes providing a library of operating parameters for a plurality of medications and step (d) includes selecting from the library the operating parameters corresponding to the medication identified from the code associated with the reservoir. In another preferred embodiment, step (c) includes reading the code from the reservoir when the reservoir is inserted into a suitable receptacle in the device.

Preferably, the apparatus releases one or more pulses at the appropriate points in the patient's inspiratory flow to optimize the deposition of the administered aerosolized medication within the desired loci within the lung. The apparatus also may adjust the controlled amount of medication delivered and/or the particle size in each dosage of medication delivered in response to detected changes in the patient's pulmonary function.

Another aspect of the invention concerns a portable, hand held device for use in delivering aerosolized medications to a patient. One such apparatus includes:

a tube forming a flow path having a mouth end and an open end;

a nozzle disposed in the tube directed toward the mouth end;

a flow transducer disposed in the inspiratory flow path for detecting the patient's breath flow including an inspiratory flow;

a receptacle for receiving a supply of aerosol generating material;

an aerosol flow path extending from the receptacle to the nozzle;

a valve interposed in the aerosol flow path for opening and closing the flow path; and means for actuating the valve to open and close the flow path for delivering an amount of aerosol out the nozzle.

In a preferred embodiment, the device further include, means for detecting the patient's inspiratory flow and operating the actuating means to deliver an amount of aerosol to the patient during the detected inspiratory flow.

In another embodiment, the device also could include means for reading a code associated with a supply of aerosol such that the medication contained in the supply can be identified and the appropriate operating parameters for that medication can be selected for controlling the valve accordingly. Preferably, the code reading means is disposed interior to the receptacle so that the code associated with the supply is read as the supply is inserted into the receptacle. Further, means for receiving a supply of power for operating the device may be disposed in the receptacle so that the receiving means can electrically connect to a source of power, e.g., a battery, associated with the supply of medication.

In another embodiment of this aspect of the invention, the valve and actuating means may be an electromechanical device, such as an integrated solenoid and valve. More preferably, the solenoid is operated to deliver the aerosol at a pulse cycle of one or more pulses to provide the aerosol with a selected particle size distribution so as to maximize the respirable fraction of the administered aerosolized compound. Also, the flow transducer is preferably a differential pressure transducer and the means for detecting the patient's inspiratory flow converts the detected differential pressures into flow measurements. In one embodiment, the flow transducer is accompanied by a laminar flow device so that the differential pressures are directly related to measured flow. In an alternate embodiment, the flow transducer does not use a laminar air flow and the detecting means uses a set of calibration constants to convert the detected differential pressures into measured flow. It should be understood, however, that most air flow paths have some degree of non-linearity which can be corrected by use of calibration constants. A filter may be provided between the mouth end of the tube and the flow transducer to prevent particulate matter from interfering with the flow measurement or clogging the flow transducer, particularly differential flow pressure transducers.

In another embodiment of this aspect of the invention, the tube, including the flow path, the flow transducer (and any filter associated therewith), a portion of the aerosol flowpath, and the nozzle may be detachable from the other portions of the device so that it may be replaced after use. In this embodiment, the aerosol flow path may be comprised of two interconnecting channels, one extending from the receptacle to a port proximate to the tube, and the other extending from that port to the nozzle.

BRIEF DESCRIPTION OF THE DRAWINGS

Further features of the invention, its nature and various advantages will be more apparent from the accompanying drawings and the following detailed description of the invention in which like reference numerals refer to like elements and in which:

FIGS. 13A–13F are collectively a flow chart of the subroutine calling chain of the software embodiment of FIG. 12 and the software appendix.

DETAILED DESCRIPTION OF THE INVENTION

Figure 1:
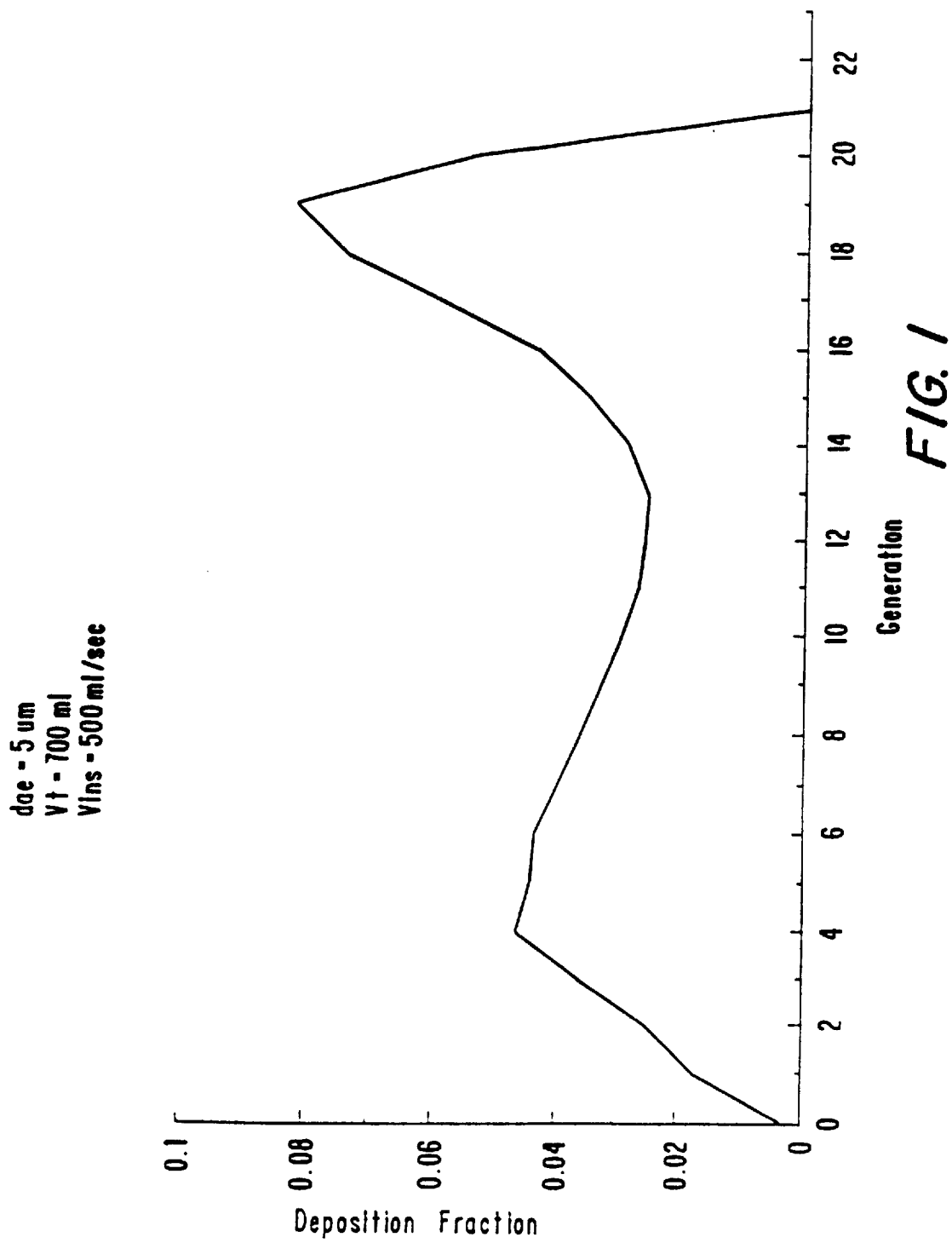
FIG. 1 is a representative plot of the predicted fraction of particles entering the trachea that deposit in each airway generation for fixed particle size and breathing pattern.
Figure 2A:
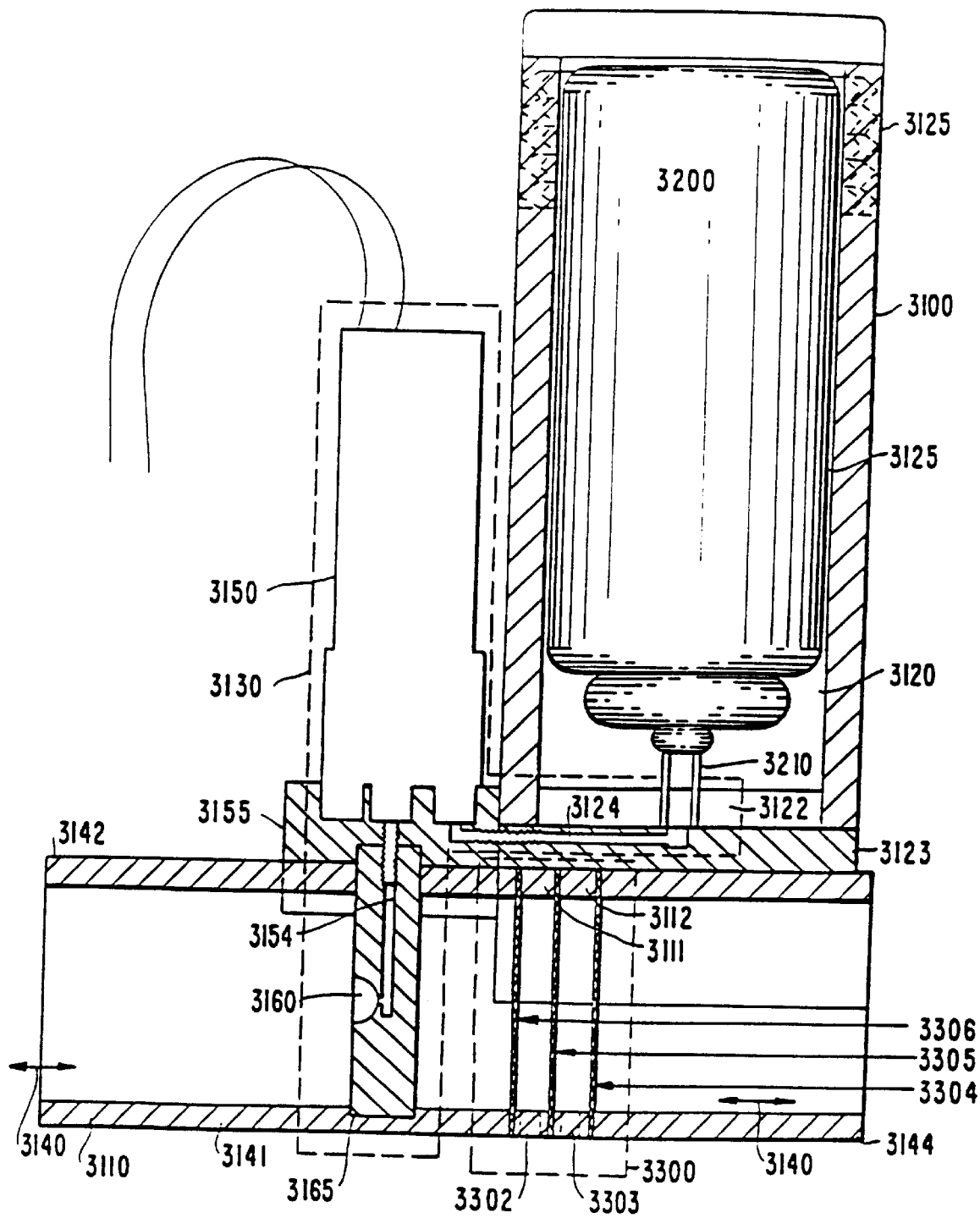
FIG. 2A is a side cross sectional view of an embodiment of the present invention.
Figure 2B:
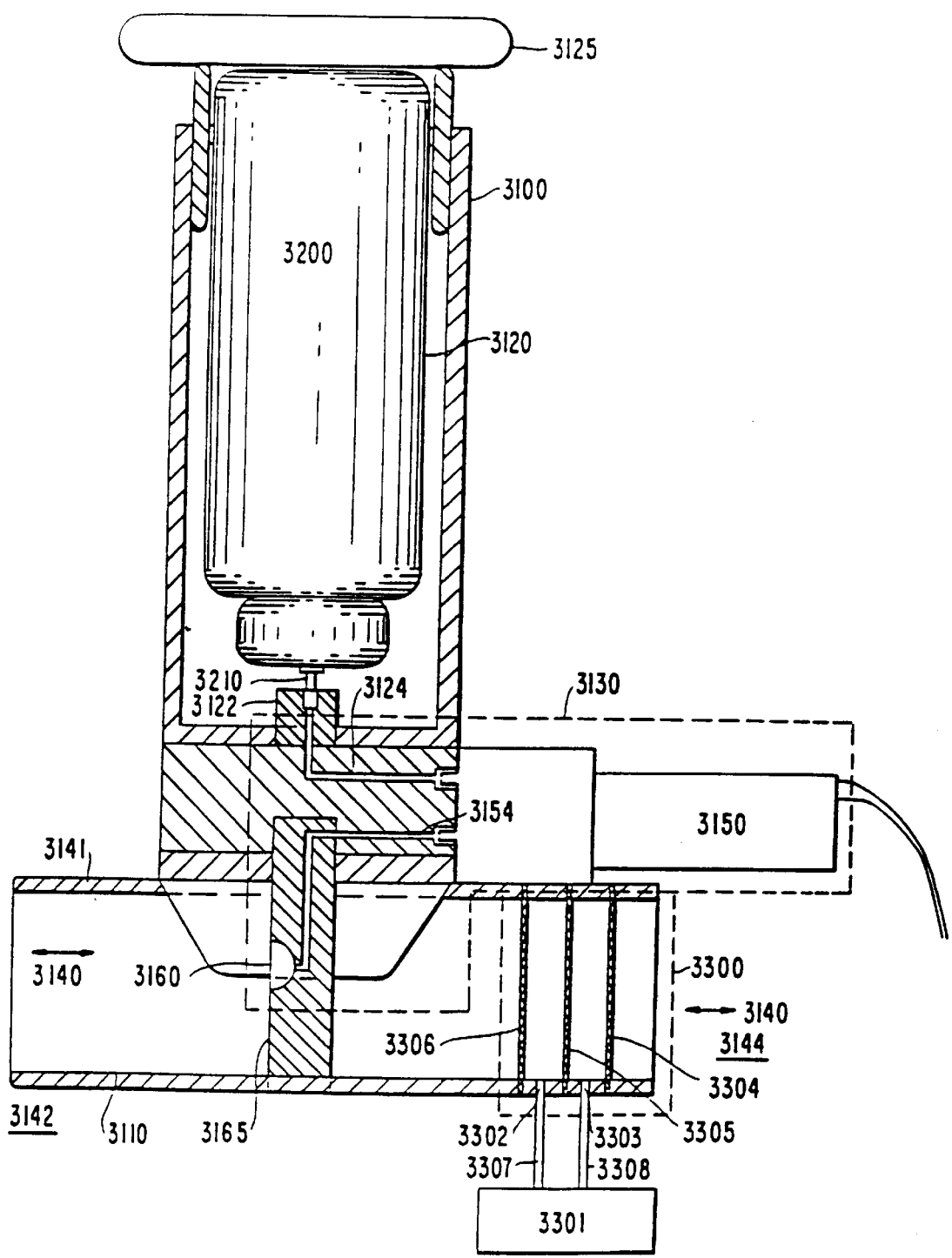
FIG. 2B is side cross sectional view of an embodiment of the present invention.
Figure 3:
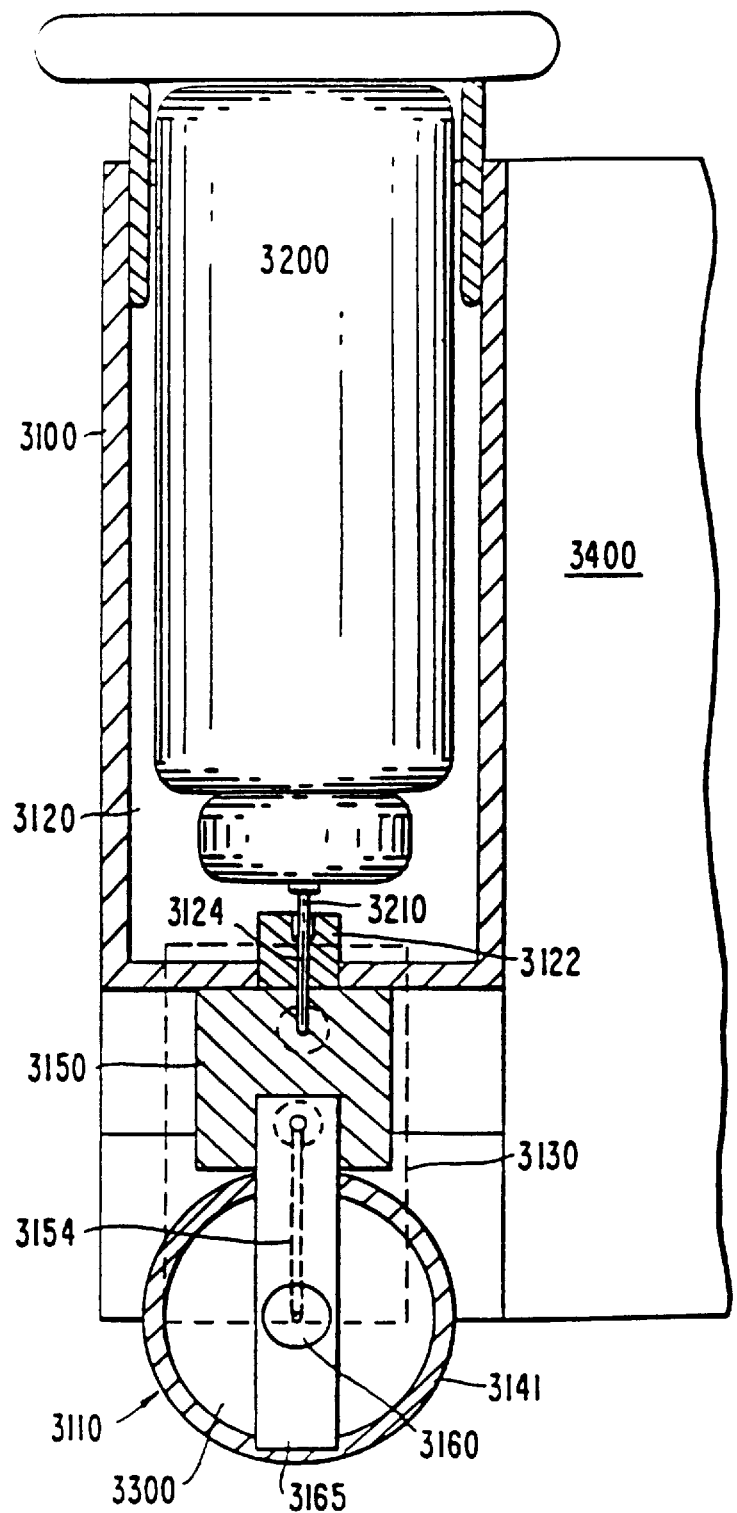
FIG. 3 is a front partial sectional view taken along line 3—3 of FIG. 2B.

Referring to FIGS. 2A, 2B, and 3, one embodiment of the present invention includes base 3100, canister 3200, flow sensor 3300, solenoid valve 3150, aerosol delivery system 3130, mouthpiece 3110, and control circuits 3400 (circuits 3400 not shown in FIG. 2A). Canister 3200 preferably contains a medication under pressure and has a valve 3210 for releasing medication. Base 3100 includes a receptacle 3120 for receiving canister 3200, a valve seat 3122 for receiving canister valve 3210, and means 3125 for retaining canister 3200 in receptacle 3120 as described herein. Means 3125 is preferably a threaded cap that screws into (FIG. 2b) or about (FIG. 2A) the open end of receptacle 3120 so that an inserted canister 3200 is fully seated in receptacle 3120 in a stationary position. In the fully seated position, canister valve 3210 is depressed open and the contents of canister 3200 are thus in communication with aerosol delivery system 3130.

Means 3125 may include alternate structures for locking canister 3200 in the fully seated position, for example, a locking hinged lid or a conventional bayonet mount connection wherein the canister body has one or more protrusions that mesh with one or more receptacles in receptacle 3120 when the canister is fully inserted and rotated in receptacle 3120.

Canister 3200 is preferably a conventional canister containing the medication to be delivered and a suitable propellant or carrier for the medication and having valve 3210 for controlling the release of medication when valve 3210 is depressed and thus opened. Such canisters 3200 are commercially available from a variety of sources and are well known in the art. One such canister is model No. C-128-S available from Prespart Co. and one suitable valve for that canister is a straight valve model no. BK-295, available from BESPAK, King's Lynn, England.

Aerosol delivery system 3130 operates under the control of control circuits 3400 and provides one or more pulses of medication from canister 3200 to airflow path 3140 and mouthpiece 3110 by selective control of solenoid valve 3150. System 3130 includes valve seat 3122, inlet channel 3124, solenoid valve 3150, outlet channel 3154, and aerosol nozzle 3160. Inlet channel 3124 forms a gas communication path between canister 3200 and solenoid valve 3150 for passing the pressurized contents of canister 3200 to valve 3150. Outlet channel 3154 forms a gas communication path from valve 3150 to nozzle 3160, for passing the pressurized contents of canister 3200 to nozzle 3160 to deliver an aerosol into air flow path 3140.

When solenoid valve 3150 is inactive or closed, inlet channel 3124 does not pass gas therethrough. Channel 3124 thus will equilibrate with the contents of canister 3200. Similarly, outlet channel 3154 does not pass gas therethrough and will equilibrate with the atmosphere. When valve 3150 is actuated or open, channels 3124 and 3154 are in open communication and the contents of canister 3200 are released to the atmosphere through nozzle 3160 to form an aerosol. Solenoid valve 3150 thus controls the delivery of the contents of canister 3200 to the patient as described further herein.

Referring to FIG. 2A, channel 3124 is tooled in manifold 3123 and manifold 3155, which respectively interface receptacle 3120 and solenoid 3150, and channel 3154 is tooled in manifold 3155 for interfacing solenoid 3150 and nozzle 3160. The use of manifolds provides for removable interconnections for repair, cleaning or replacement of parts of Base 3100.

Air flow path 3140 is formed of a tube 3141, preferably having a flattened cylindrical cross section, and includes a mouthpiece 3110 at mouth end 3142 and flow sensor 3300 at back end 3144. Interposed between mouth end 3142 and back end 3144 is a projection 3165 which contains nozzle 3160 and is secured to the wall of air flow path 3140. Projection 3165 is provided with a dimension that does not interfere with flow through path 3140 and preferably extends diametrically across flow path 3140 so that nozzle 3160 is directed to release an aerosol into and in longitudinal alignment with air flow path 3140 for inspiration by the patient. Projection 3165 is preferably made of the same material as tube 3141 forming flow path 3140, e.g., an acrylic material, and more preferably is molded as a part of tube 3141. Nozzle 3160 is preferably provided with a configuration that facilitates aerosol generation and dispersion appropriate for the tube dimensions.

Tube 3141 preferably provides mouthpiece 3110 with a cylindrical cross section preferably larger than the aerosol plume delivery into the patient's mouth. Tube 3141 need not have a uniform cross section, but desirably has minimal pressure drop there across (excluding any pressure drop across sensor 3300). Alternate embodiments for the cross section of mouth end 3142 may include circular, oval or flattened oval cross sections or other configurations developed to provide a good seal between the patient's mouth and flow path 3140 so that the patient's inspiratory and expiratory flow passes substantially through tube 3141 along path 3140.

Flow sensor 3300 may be any sensor that provides a measure of flow at a rate of from about 0 to about 800 liters per minute. Flow sensor 3300 is located in flow path 3140 where it will not interfere with the delivery of aerosol to the patient, yet is able to measure both inspiratory and expiratory flow. In the preferred embodiment, sensor 3300 includes a flow resistor device that provides laminar air flow across sensor 3300, comprising three screens, 3304, 3305, and 3306, and two pressure ports 3302 and 3303. Associated with sensor 3300 are a conventional pressure differential transducer 3301 and circuits for obtaining a flow measurement (see FIGS. 4 and 6, transducer 3301 is illustrated in FIG. 2B for reference). Screens 3304, 3305 and 3306 are oriented perpendicular to air flow path 3140, spaced apart ¼" in parallel and secured to the inside of tube 3141 so that they extend across the cross sectional area of path 3140. Referring to FIG. 2A, tube 3141 is assembled by gluing together, in axial alignment, mouth tube section 3110, screen 3306, tube section 3111, screen 3305, tube section 3112, screen 3304, and end tube section 3144 whereby the lengths of tube sections 3111 and 3112 define the spacing between the screens.

Screen 3305 is a resistor screen across which a differential pressure is measured at ports 3302 and 3303 to obtain a measure of the flow rate. Screens 3304 and 3306 provide a laminar air flow across screen 3305 and through sensor 3300 which is suitable for obtaining air flow measurements. Port 3302 is located between screens 3306 and 3305, and port 3303 is located between screens 3305 and 3304. Referring to FIG. 2B, ports 3302 and 3303 are respectively connected to transducer 3301 by conventional flexible tubes 3307 and 3308 having about a 3 mm inner diameter and provide the differential pressures developed across resistive screen 3305 to transducer 3301. The differential pressures, preferably in the range of plus or minus 10 cm of water, are then used to provide a voltage proportional to flow through path 3140, and the sign of the voltage determines the direction of flow. One such preferred differential flow transducer 3301 is model No. NPH-8-2.5DH, commercially available from NOVASENSOR of Fremont, Calif. The flow through pathway 3140 may be sampled at 60 Hz to obtain the flow rate measurements.

Other forms of such a sensor 3300 may be other forms of a pneumotachograph, e.g., a temperature compensated device, or a thermal wire air flow measurement system. A pneumotachograph is a known sensor having a pneumatic resistor interposed in an air flow, such as a resistor screen, that maintains a laminar air flow having a pressure drop across the structure. The pressure drop is measured and can be directly related to air flow rates across the structure by the pneumatic equivalent of Ohm's law. Thus, once the sensor is calibrated, the air flow rate can be accurately determined based on the measured pressure drop for any air flowing across the structure within the operating range of the sensor.

In an alternate embodiment (not shown), a suitable differential pressure flow sensor could include, for example, a venturi device or a flow resistive screen not characterized by laminar flow, provided that the raw differential pressure measurement obtained across such a venturi device or the flow resistor is calibrated to account for the non-linearity of the air flow path so that the calibrated flow data correspond to data from a linear flow path.

In the preferred embodiment, flow path 3140, including mouthpiece 3110, protrusion 3165, and sensor 3300 (optionally not including transducer 3301) may be removable from body 3100 so that it may comprise a disposable part. A conventional detachable connection, not shown, may be provided. Accordingly, means for interconnecting channel 3154 to valve 3150, such as a male-female snap connection, may be incorporated into the design. Use of a disposable airway is desirable because debris will accumulate on the part so that it can be cleaned or a new mouthpiece provided. Similarly, if a filter is provided (not shown), that filter may be separately removable from the part for replacement.

Referring to FIGS. 2, 3, 4, and 5, control electronics 3400 for an embodiment of the present invention are shown. Electronics 3400 include a microprocessor 2000, an external memory subsystem 2100, a decoder circuit 2020, a latch device 2030, a reset circuit 2040, a clock oscillator 2010, a data acquisition subsystem 2200, three LED annunciator subsystems 2300, 2400 and 2500, a solenoid actuator subsystem 2600, an audio speaker subsystem 2700, and a character display subsystem 2800. The discrete components of electronics 3400 are conventional parts having input and output pins which are configured as illustrated in FIGS. 4–11 and described herein, which connections are made in accordance with the instructions provided by the device manufacturers, unless otherwise stated.

Use of CMOS technology for electronics 3400 is preferred because of the low power consumption of such devices. This permits the use of a battery powered, portable, hand-held device for patient use having a size that compares favorably to existing metered dose inhaler devices.

Microprocessor 2000 is provided with suitable software programming that controls the operation of the device. One embodiment of such software is set forth as a software appendix to this specification and is discussed below.

Optionally, electronics 3400 may include a voltage converter and an associated output port for converting the digital information to a voltage format compatible for communicating with another microprocessor device, for example, an RS232 port or a facsimile machine (not shown). Further, as discussed in detail below, electronics 3400 may include means for reading a canister code for identifying the contents of the medication to be administered and selecting the device administration protocol for the identified medication (not shown).

Figure 4:
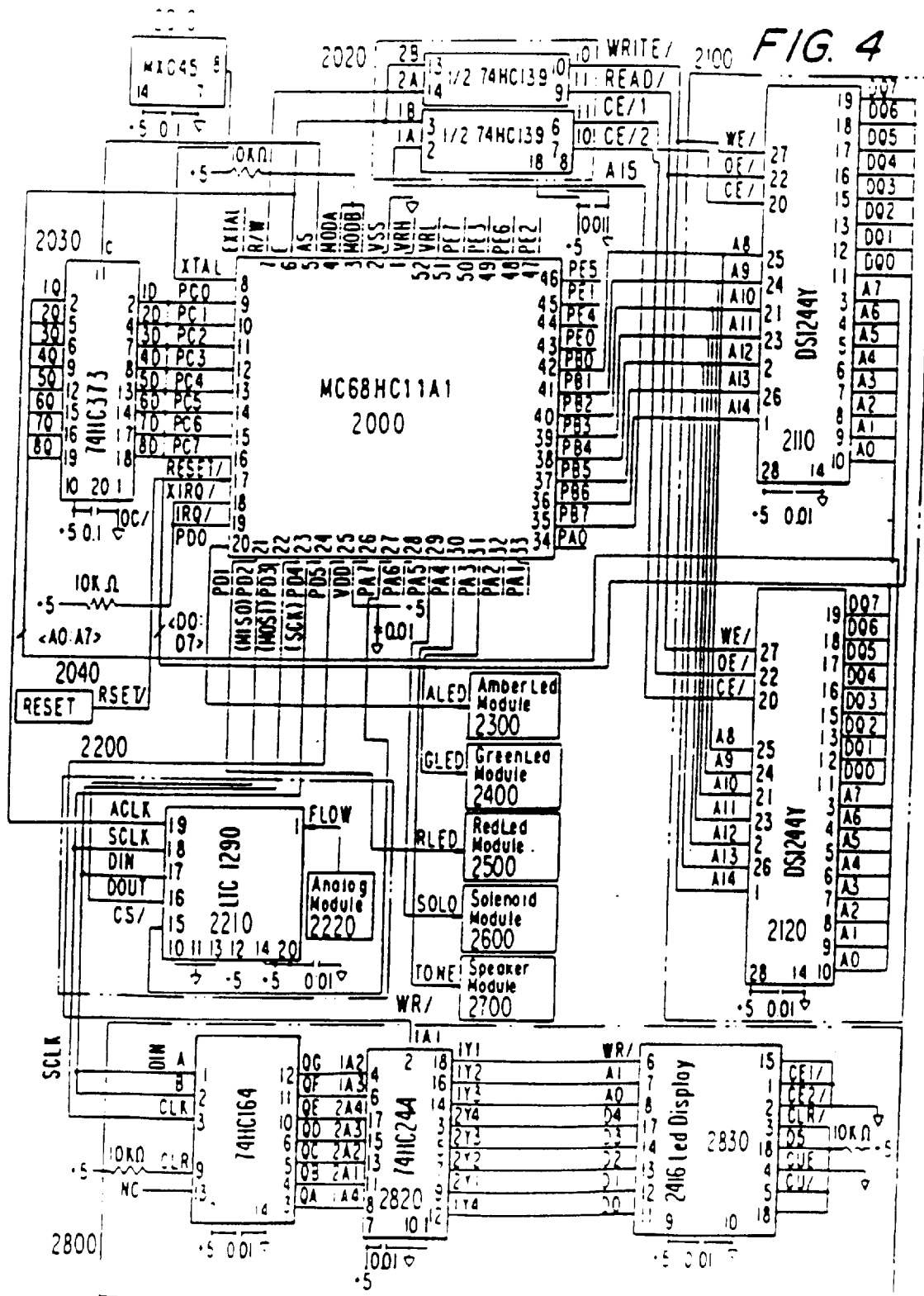
FIG. 4 is a schematic diagram of the digital control circuits of the device of FIG. 2B.

Referring to FIG. 4, microprocessor 2000 may be any software controlled device suitable for operating the data acquisition and determination functions and for controlling the operation of solenoid valve 3150 to release the selected number of pulses of medication at the desired points in the patient's inspiratory flow in accordance with the preferred embodiment of the invention. One suitable device for microprocessor 2000 is model no. MC68HC11A1, available from Motorola, Inc., Microcontroller Division, Austin, Tex., the use of which is described herein.

Microprocessor 2000 is preferably configured to run in an expanded multiplexed mode through connection of lines MODA and MODB at pins 2 and 3 to logic one, a reference voltage Vcc of +5 volt fed across a 10 KΩ resistor. Latch device 2030 is preferably an 8 bit device that demultiplexes the address and data information transmitted along port c at pins 9–16 of microprocessor 2000 and allows addressing of the address space of memory subsystem 2100. Latch 2030 is preferably model 74HC373, available from National Semiconductor, Santa Clara, Calif.

Memory subsystem 2100 preferably has a 64K byte address space and includes two 32K byte non-volatile CMOS RAM devices 2110 and 2120, each containing an internal lithium battery. Preferably, RAM devices 2110 and 2120 each contain a non-volatile clock/calendar that is settable and accessible under software control by microprocessor 2000. In the preferred embodiment, only the clock/calendar of device 2110 is used. Non-volatile RAM devices 2110 and 2120 thus provide for maintaining a date and time record of the data acquired and the operation of the device for subsequent review and evaluation by appropriate medical practitioners. This will enable evaluation of the performance of the device for the delivery of medication and the efficacy of the drug therapy program for the patient, even in the event of general power loss of electronic control circuits 3400. The clock/calendar feature also can be used to perform the alarm clock feature to indicate to the patient that a dose is to be administered, for example, by reviewing a list of scheduled dosing times. Appropriate RAM devices 2110 and 2120 are preferably models DS1244Y, available from Dallas Semiconductor, Dallas, Tex.

The 64K byte address space of memory subsystem 2100 may be continuously addressed in the following manner. Signal AS at pin 4 of microprocessor 2000 causes the low 8 bits of a 16 bit address to be latched from port c at pins 9–16 of microprocessor 2000 into pins 2, 4, 7, 8, 13, 14, 17, and 18 of latch 2030. The latching of these address bits into latch 2030 allows 8 bits of data from port c, the high address bits from port b (pins 35–42 of microprocessor 2000) and the low 8 address bits from the output at pins 2, 5, 6, 9, 12, 15, 16, and 19 of latch 2030 to be available simultaneously.

Decoder device 2020 is used to decode the write enable WE/, output enable OE/, and chip enable CE/ control lines at pins 27, 22, and 20 respectively of each of RAMs 2110 and 2120. A suitable decoder device 2020 is model 74HC139, available from National Semiconductor, Santa Clara, Calif. Address line A15 from line PB7 at pin 35 of microprocessor 2000, is input to line 1A at pin 2 of decoder 2020 and is used to determine which 32K byte RAM bank to select for each memory access. Valid WRITE/, READ/, CE/1, and CE/2 signals respectively coming from pins 10, 9, 6, and 7 of decoder 2020 are all active low and are valid only when the signal E from pin 5 of microprocessor 2000 is raised active high. This procedure ensures that memory subsystem 2100 will be accessed only during valid memory references.

Clock 2010 provides a clock input for microprocessor 2000. Preferably, clock 2010 is a CMOS oscillator having a frequency of 8.0 MHz. A suitable device for clock 2010 is model MX045, available from CTS Inc., Japan.

Figure 5:
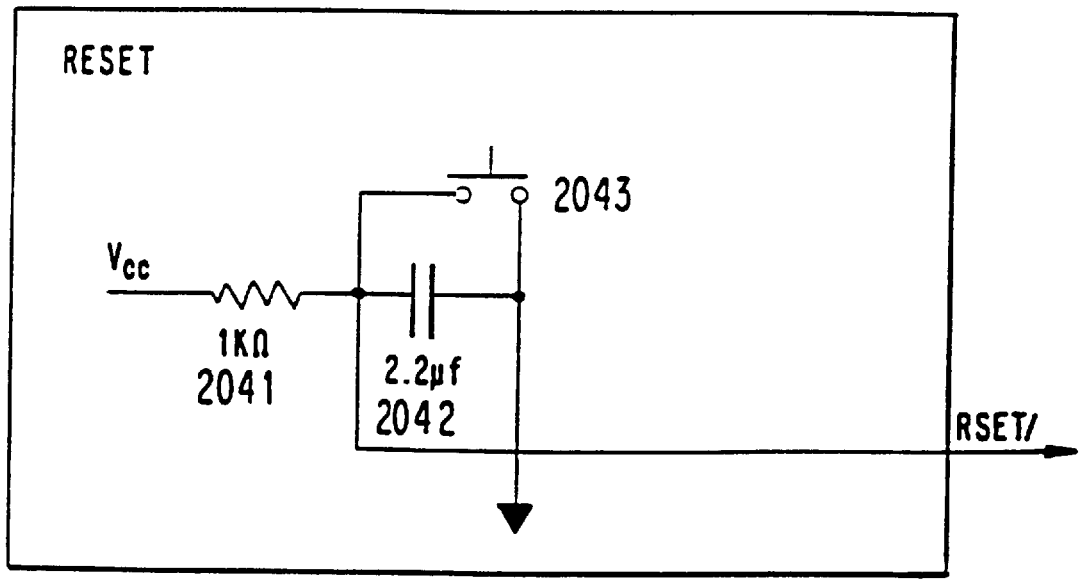
FIG. 5 is a schematic diagram of a reset circuit of FIG. 4.

Referring to FIGS. 4 and 5, reset circuit 2040 provides a power-on reset function. Reset circuit 2040 includes a reference voltage Vcc, resistor 2041, capacitor 2042 and switch 2043. When the system is turned on, a transient pulse from ground to voltage Vcc is generated. Vcc is preferably +5 volts, resistor 2041 is preferably 1 KΩ, and capacitor 2042 is preferably 2.2 microfarads. Resistor 2041 thus presents a logic high signal to the non-grounding lead of capacitor 2042 when power is applied to the system. However, the potential across capacitor 2042 does not change instantaneously and a ground potential is presented to the RESET/ line at pin 17 of microprocessor 2000 until capacitor 2042 charges. This provides for a reset of microprocessor 2000, its software routines, and the electronic system of the device. A manual reset may be obtained at an arbitrary time by closing switch 2043. This provides for discharging capacitor 2042 to obtain a transient ground pulse for resetting microprocessor 2000.

Referring to FIGS. 4–11, microprocessor 2000 is configured to be connected to and control data acquisition subsystem 2200, LED annunciator modules 2300, 2400, and 2500, solenoid control module 2600, speaker module 2700, and character display subsystem 2800.

Figure 6:
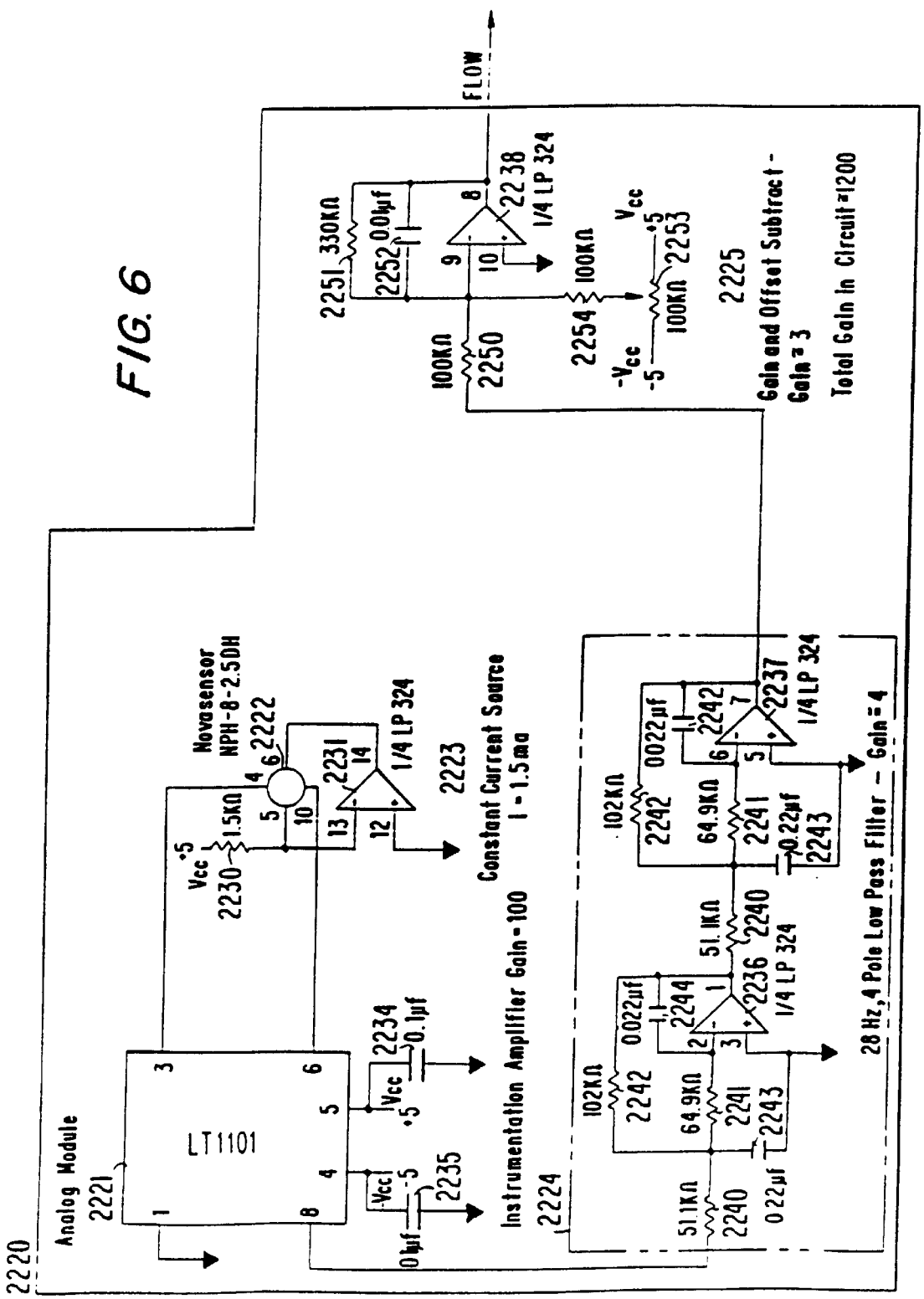
FIG. 6 is a schematic diagram of the analog module of FIG. 4.
Figure 7:
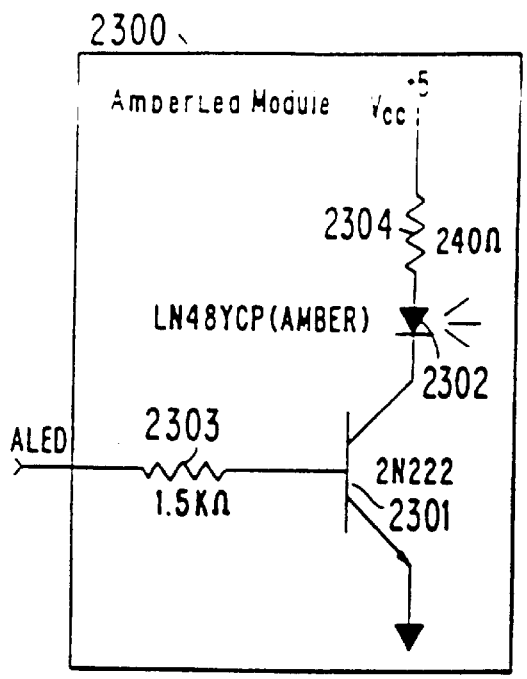
FIG. 7 is a schematic diagram of an LED annunciator module of FIG. 4.
Figure 8:
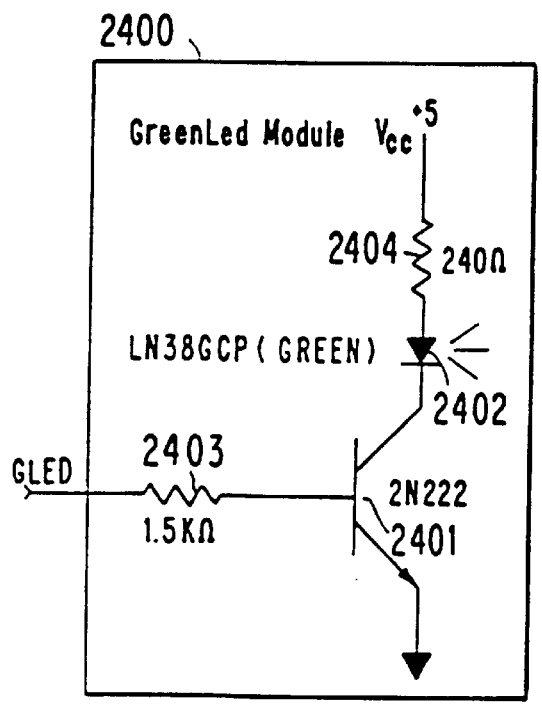
FIG. 8 is a schematic diagram of an LED annunciator module of FIG. 4.
Figure 9:
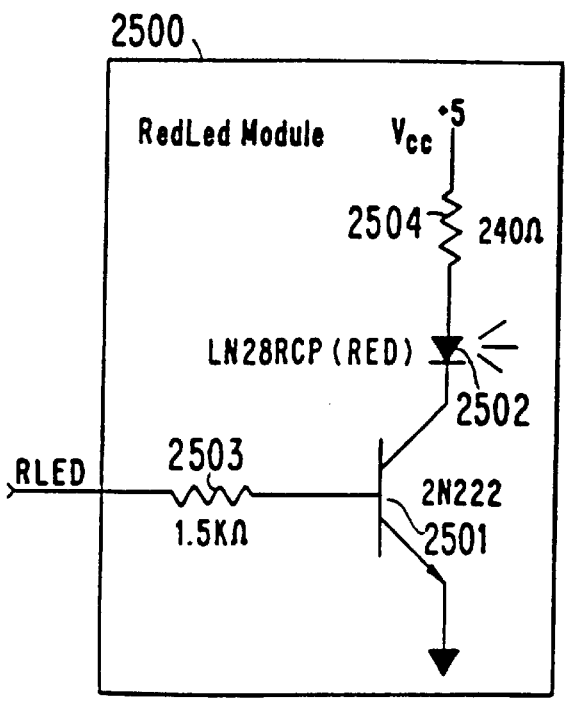
FIG. 9 is a schematic diagram of an LED annunciator module of FIG. 4.

With reference to FIGS. 4 and 6, data acquisition subsystem 2200 includes a 12 bit analog to digital converter (ADC) 2210 and an analog circuit 2220. ADC 2210 is preferably a model LTC1290, available from Linear Technology Corporation, Milpitas, Calif. and is interfaced to microprocessor 2000 via a three wire serial interface and a chip select line. The serial interface includes control lines serial clock SCLK, data in DIN, and data out DOUT, respectively at pins 18, 17, and 16 of ADC 2210. These control lines are connected to lines serial clock SCK, master out slave in MOSI, and master in slave out MISO at pins 24, 23, and 22 of microprocessor 2000.

Lines SCK, MOSI and MISO of microprocessor 2000 are internally associated with the serial peripheral interface (SPI) feature of microprocessor 2000 which is programmed to run as "master" in this embodiment. The SPI allows a stream of bytes of arbitrary length to be simultaneously sent and received by microprocessor 2000. Bytes sent serially to the DIN input of ADC 2210 are interpreted as digitized data points.

Input CS/ at pin 15 of ADC 2210 is connected to line A7 at pin 27 of microprocessor 2000 and is manipulated under software control to facilitate communication to and from ADC 2210. A logic low signal on this line causes data to be simultaneously shifted in and out of lines DIN and DOUT, respectively. A logic high signal on this line cause ADC 2210 to ignore data present on line DIN and causes the DOUT line to float.

Analog module 2220 generates a voltage proportional to flow across sensor 3300 as determined by a differential strain gage pressure transducer 2222. Module 2220 includes an instrumentation amplifier 2221, pressure transducer 2222 (corresponding to element 3301 illustrated in FIG. 4), a constant current source 2223, a low pass filter circuit 2224, and a gain and offset circuit 2225.

Transducer 2222 is preferably a wheatstone bridge strain gage pressure transducer capable of producing a signal over a pressure range of plus or minus 10 inches of water. One such transducer device is model NPH-8-02.5DH available from Novasensor Inc., Fremont, Calif. Transducer 2222 is excited by constant current source 2223, an operational amplifier 2231 configured to provide approximately 1.5 ma. Input to transducer 2222 are the pressures communicated through tubes 3307 and 3308 from ports 3302 and 3303 of sensor 3300 which are converted to electrical signals by transducer 2222. The output electrical signals produced at pins 4 and 10 of transducer 2222 are provided to input pins 3 and 6 of instrumentation amplifier 2221. Input at pin 5 of transducer 2222 is a reference voltage Vcc of +5 volts fed across a resistor 2230 having a resistance of 1.5 KΩ.

Instrumentation amplifier 2221 is preferably a model LT1101 available from Linear Technology, Fremont, Calif., and is configured with a reference voltage −Vcc of −5 volt input to pin 4, and a reference voltage Vcc of +5 volts input to pin 5, respectively fed across parallel decoupling capacitors 2233 and 2234 each having a capacitance of 0.1 microfarads. Amplifier 2221 provides a gain of about 100.

The outputs at pins 1 and 8 of amplifier 2221 are fed forward to filter 2224. Filter 2224 is configured as a 28 Hz, 4 pole active low pass filter having a gain of about 4. This circuit acts as an anti-aliasing filter prior to the anticipated 60 Hz sampling rate of analog to digital conversion. Filter circuit 2224 includes two operational amplifiers 2236 and 2237 having identical circuit configurations that are connected in series as illustrated in FIG. 6. Resistors 2240 are 51.1 KΩ, resistors 2241 are 64.9 KΩ. Resistors 2242 are 102 KΩ. Capacitors 2243 are 0.22 microfarads and capacitors 2244 are 0.022 microfarads.

The filtered output signal is passed through circuit 2225 to offset adjust the signal for a final gain of about 1200. Circuit 2225 includes amplifier 2238 configured as illustrated in FIG. 6. Resistor 2250 is 100 KΩ, resistor 2251 is 330 KΩ, capacitor 2252 is 0.01 microfarads, resistor 2254 is 100 KΩ, and potentiometer 2253 has a maximum resistance of 100 KΩ. Potentiometer 2253 is preferably a conventional multiturn potentiometer that provides for nulling the offset prior to beginning any flow measurement. The function could be provided by a digitally controlled potentiometer under software program control. The four operational amplifiers of circuit 2220 are preferably contained within a single device, part No. LP324, available from National Semiconductor, Santa Clara, Calif.

The differential pressure inputs of transducer 2222 are in communication with airway 3140 through port 3302 and 3303 via tubes 3307 and 3308. Thus, in operation, air flow through sensor 3300 causes a pressure drop across resistor screen 3305 that varies with the flow. Analog module 2220 thus provides an output signal FLOW having a voltage proportional to flow and a sign, plus or minus, that indicates the direction of flow being detected.

Output FLOW of circuit 2220 is fed to pin 1 of ADC 2210 via channel 1 of the internal analog multiplexor. This input is configured under program control to function in a bipolar, singled ended mode.

Referring to FIGS. 4 and 7–9, LED annunciator modules 2300, 2400, and 2500 are similarly configured and each includes respectively one transistor switch 2301, 2401, and 2501 controlling a single light emitting diode 2302, 2402, and 2502, where each of diodes 2302, 2402 and 2502 emit light at a different color of the visible spectrum, more particularly amber, green and red respectively. Appropriate LEDs are part numbers LN48YCP (amber), LN48GCP (green) and LN48RCP (red), each available from Panasonic, Japan.

For each of modules 2300, 2400 and 2500, each switching transistor is driven, via a base current limiting resistor, by the corresponding digital output at each of pins 20, 31, and 21 of microprocessor 2000. When the transistor conducts, current flows through the LED to ground through a collector current limiting resistor. Each of the circuits are respectively configured with transistors 2301, 2401, and 2501 having base resistors 2303, 2403, and 2503 of 1.5 KΩ, LEDs 2302, 2402, and 2502 in series with collector resistors 2304, 2404, and 2504 each having 240 Ω in series with reference voltage Vcc of +5 volts, and the transistor emitters tied to ground.

Figure 10:
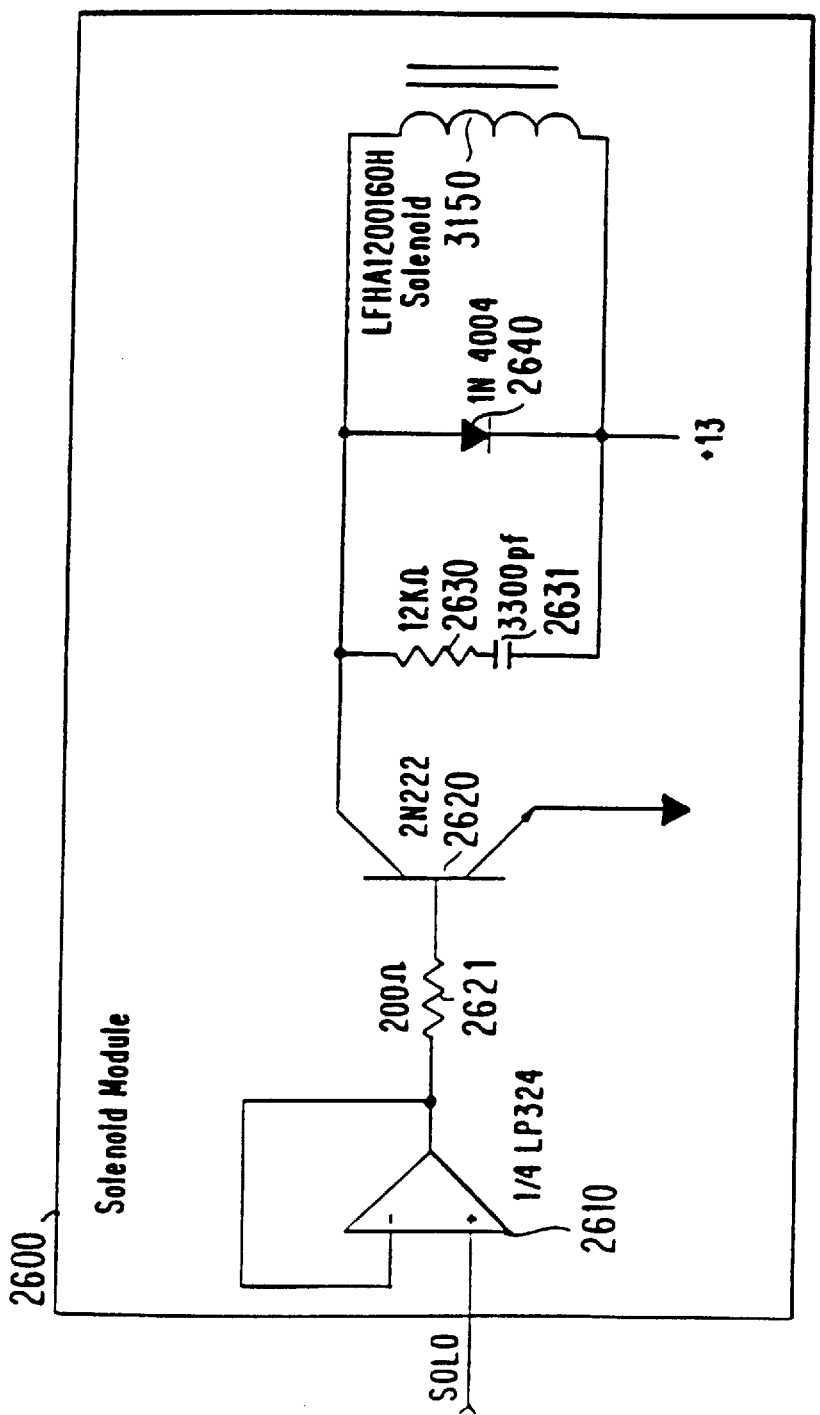
FIG. 10 is a schematic diagram of the solenoid control module of FIG. 4.

Referring to FIGS. 4 and 10, microprocessor 2000 controls the operation of solenoid valve 3150 under software control through module 2600. In operation, module 2600 causes solenoid valve 3150 to deliver a pulse of aerosolized medication when the digital output line PA5 at pin 29 of microprocessor 2000, delivered to module 2600 as line SOLO, is brought high. Module 2600 includes amplifier 2610, current limiting base resistor 2621 (200 Ω), switching transistor 2620, resistor 2630 (12 KΩ) and capacitor 2631 (3300 picofarads) connected in series, and collectively in parallel with diode 2640 and in parallel with the inputs of solenoid valve 3150 as illustrated in FIG. 10. Solenoid valve 3150 is preferably model No. LFHA1200160H, available from Lee Corporation, Westbrook, Conn., and includes an integral solenoid and valve mechanism wherein the valve is operated by the solenoid. Amplifier 2610 is preferably an amplifier from device model LP324 available from National Semiconductor, Santa Clara, Calif., and is configured in a voltage follower mode. The combination of resistor 2630, capacitor 2631 and diode 2640 suppresses surges during the firing of solenoid valve 3150. Diode 2640 is preferably a conventional model No. 1N4004 diode.

When input signal SOLO is brought high, transistor 2620, preferably a model 2N222 available from Motorola, Inc, Phoenix, Ariz., conducts to cause current to flow through solenoid valve 3150. This causes valve 3150 to open to release a dosage of medication from canister 3200 through flow system 3130 for delivery to and inspiration by the patient. When signal SOLO is brought low, the current stops and valve 3150 closes, terminating the dosage pulse. In accordance with the present invention, the operation of the solenoid valve 3150 is controlled by microprocessor 2000 under software control to provide for improved delivery of aerosolized drugs to the patient's lungs.

Figure 11:
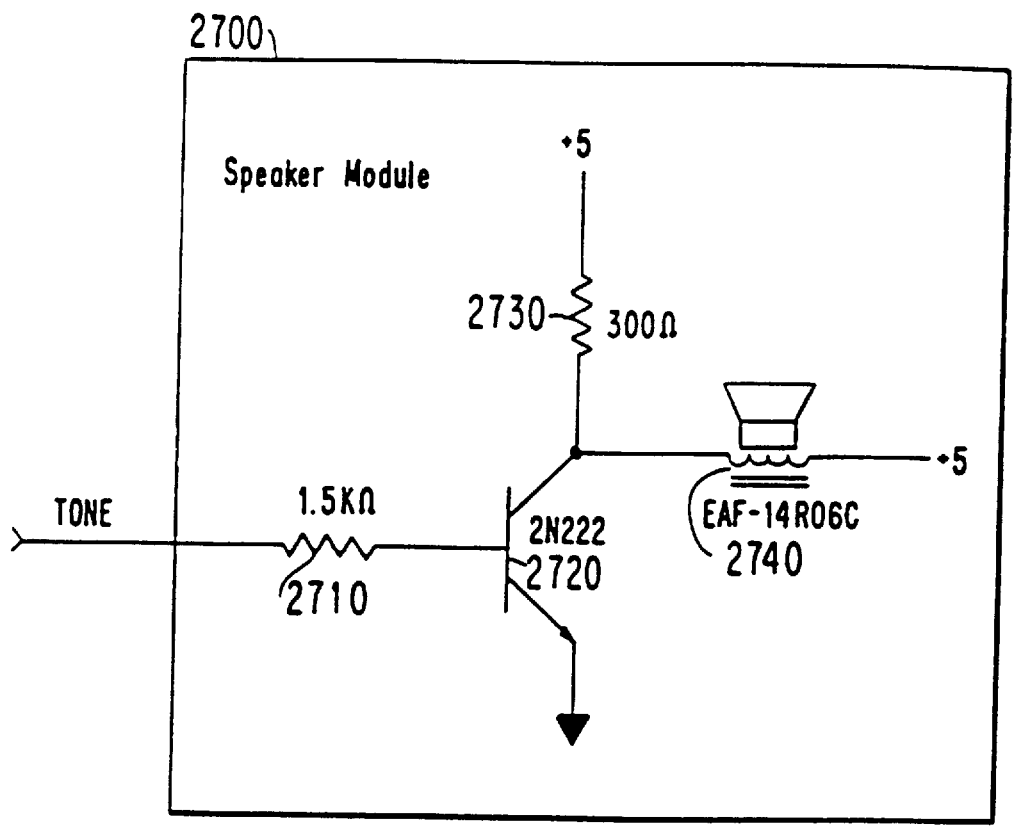
FIG. 11 is a schematic diagram of the speaker module of FIG. 4.

Referring to FIGS. 4 and 11, speaker module 2700 is a one transistor amplifier controlling an audio transducer 2740. A preferred transducer 2740 is model No. EAF-14RO6C, available from Panasonic, Japan. Module 2700 includes transistor 2720, preferably a model 2N222 available from Motorola, Inc., Phoenix, Ariz., configured with a base current limiting resistor 2730 having 1.5 KΩ, a reference voltage Vcc of +5 volts fed across, in parallel, collector resistor 2730 having 300 Ω and audio transducer 2740. The transistor emitter is grounded. Input to module 2700 is signal TONE from line PA4 at pin 30 of microprocessor 2000. When transistor 2720 conducts, current flows through collector resistor 2730 and speaker 2740 through the collector of transistor 2720. The current through speaker 2740 is thus the collector current of transistor 2720 when saturated minus the current through resistor 2730. Line PA4 of microprocessor 2000 will be switched under program control so as to introduce a square wave of varying period to the input signal TONE. In this manner, an audible tone proportional to airway flow will be generated.

The audible tone is useful for cuing the patient to breathe in consistent patterns from time to time. In an alternate embodiment, a learning sequence can be programmed into microprocessor 2000 whereby a preselected signal TONE is generated to teach the patient to breath in accordance with a desired breathing pattern for optimal delivery of the particular drug to be administered. Thus, the flow detected can be compared to the preselected signal TONE such that feedback techniques, e.g., using the LED modules, can be use to train the patient to breath in a desirable manner.

In alternate embodiments, speaker 3740 could be replaced by a piezoelectric sheet or material capable of producing audible vibrations or tactile vibrations, the latter being particularly useful for deaf patients.

Referring to FIG. 4, character display subsystem 2800 allows bytes of numeric character data to be sent via the SPI of microprocessor 2000 to a multisegment LED character display 2830. A preferred display 2830 is a model No. NSM2416, available from National Semiconductor, Santa Clara, Calif. The byte representing a single character to be displayed is sent to shift register 2810 via the SPI of microprocessor 2000. This serial interface is configured in a unidirectional manner so that data can be provided by microprocessor 2000 but no data can be sent to microprocessor 2000 over line MISO. All data sent over the SPI will appear on input line DIN at pins 1 and 2 of shift register 2810 and will be clocked in. However, data will only be loaded into display 2830 when the digital output line PD5 at pin 25 is asserted by being brought low. Each byte sent to shift register 2180, preferably model no. 74HC164, available from Motorola, Inc., Phoenix, Ariz., intended for character display must contain the ASCII code of the character to be displayed in bits <0:4> and the two bit position address (00=display position 0; 11=display position 3) of the display location in which the character is to appear in bits <5:6>. The most significant bit (bit <7:7>) is ignored. The outputs of shift register 2810 and display 2830 select line are conditioned by buffers 2820, (preferably part No. 74HC244, available from National Semiconductor, Santa Clara, Calif.). This is done to allow CMOS level signals from microprocessor 2000 and shift register 2810 to drive inputs of the TTL display 2830.

In an alternate embodiment, display module 2800 may be configured under appropriate software instruction (not shown) and with additional hardware and wire connections so that the full set of ASCII coded bits can be transmitted for providing visual prompt alphanumeric information to the patient and to display various measured parameters to the patient and the medical examiner. Such a display module 2800 could be used to instruct the patient how to use the device for measuring a pulmonary function, specifically FEV1, or to obtain a desirable inspiratory flow. These instructions could include, for example, "take a breath now" indicating that the device is ready, "hold your breath longer" during an inspiratory pause period or other messages, for example, whether or not to breath harder on expiration. Thus, in addition to displaying the number of does remaining, display module 2500 can be used on the one hand to prompt the patient to breathe in accordance with selected flow patterns for measuring specific pulmonary functions, and on the other hand to prompt the patient to breathe consistently from breath to breath and thus optimize use of the device for the intended drug therapy.

Further, display module 2800 also could be used under appropriate software programming (not shown) to display the amount of medication dispensed or given effectively, which may differ from the amount dispensed and the amount of medication remaining, and provide a clinical acuity index more detailed than that provided by LED annuciator modules 2300, 2400 and 2500. Also, display module 2800 be used to instruct the patient to contact the medical examiner in the event of a determined lack of improvement in the patient's measured pulmonary functions over a predetermined period of time during the course of treatment, a determined decline in condition or a repeated inability to deliver medication in either or both of ProgBreathMode or CalBreathMode (as described below).

Similarly, display module 2800 can provide the patient alphanumeric information regarding the times and dates medication is to be administered, battery condition, and diagnostics for the condition and operation of the device, and, in conjunction with microprocessor 2000 and speaker 2740, generate a tone when the conditions require servicing the device or a battery needs to be changed.

Referring to FIGS. 12 and 13A–13E and the software appendix, a software flowchart and subroutine calling chain corresponding to the program of the software appendix are illustrated. Subroutines 100 automatically perform system initialization on Reset. Control then transfers to system main loop IdleLoop 000 which repetitively executes subroutines CheckAlarm 200, GetDataPoint 300, CheckThreshold 400, IntegrateOn 500, LoggingOn 600, ProcessBreath 700, IntegrateOff 1000, and LoggingOff 1010, in accordance with the algorithm described below, forever.

Subroutine 200 checks the system's real time clock and compare the current time (in hours) to a stored list of recommended dosing times for the patient and the selected medication. If the current hour appears on this list, subroutine 210 causes microprocessor 2000 to provide a signal TONE to generate an audible alarm on module 2700 once for that hour. In the present embodiment the alarm serves as a recommendation to the patient that a dose is to be taken, but does not control or alter the function of the rest of the program. After the alarm clock functions have been performed, control transfers to subroutine GetDataPoint at branch point 300 which measures the instantaneous flow in airway 3140.

Figure 12:
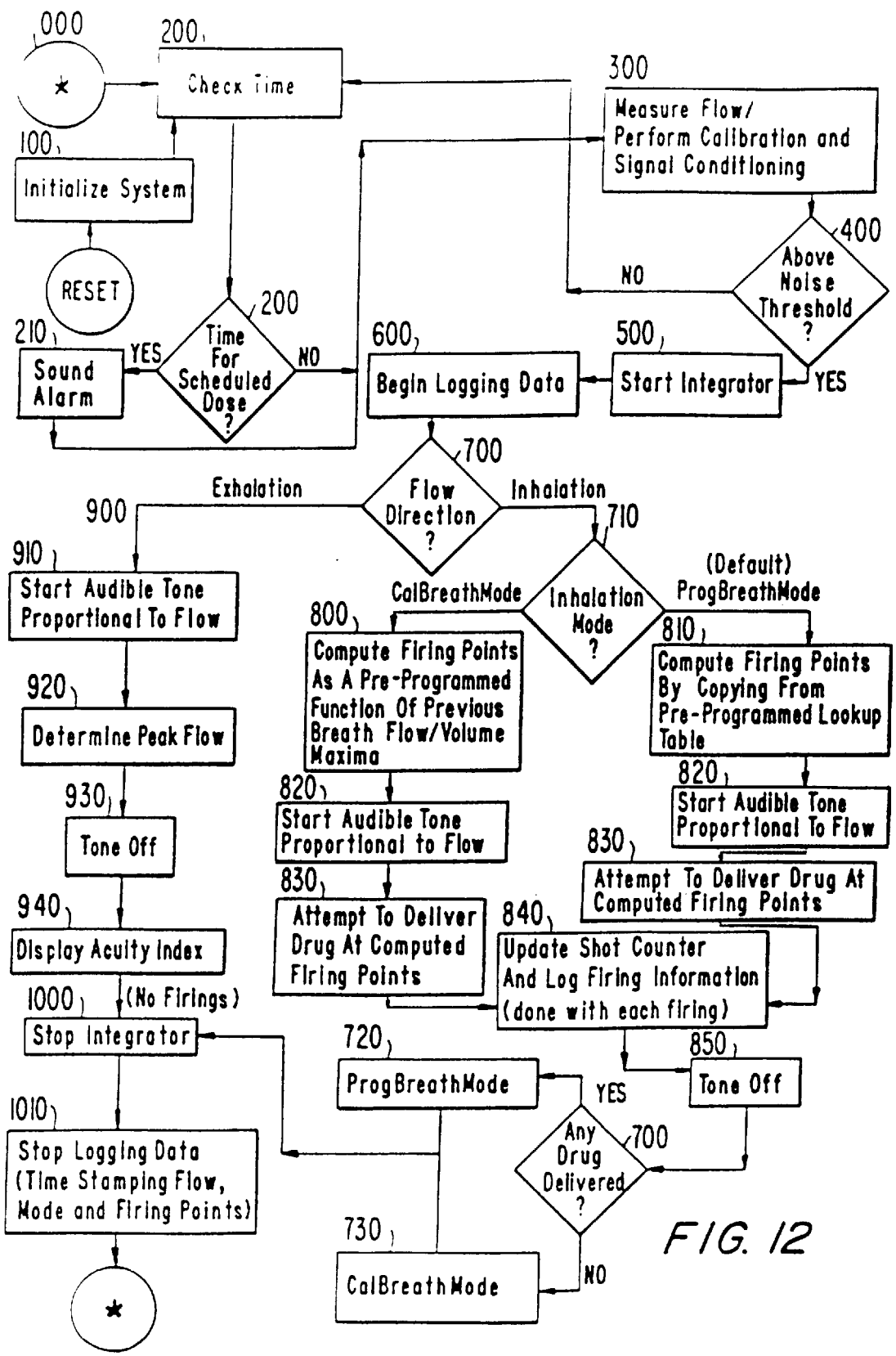
FIG. 12 is a flow chart of the software of a preferred embodiment of the device of FIG. 4 in accordance with the present invention.
Figure 13A:
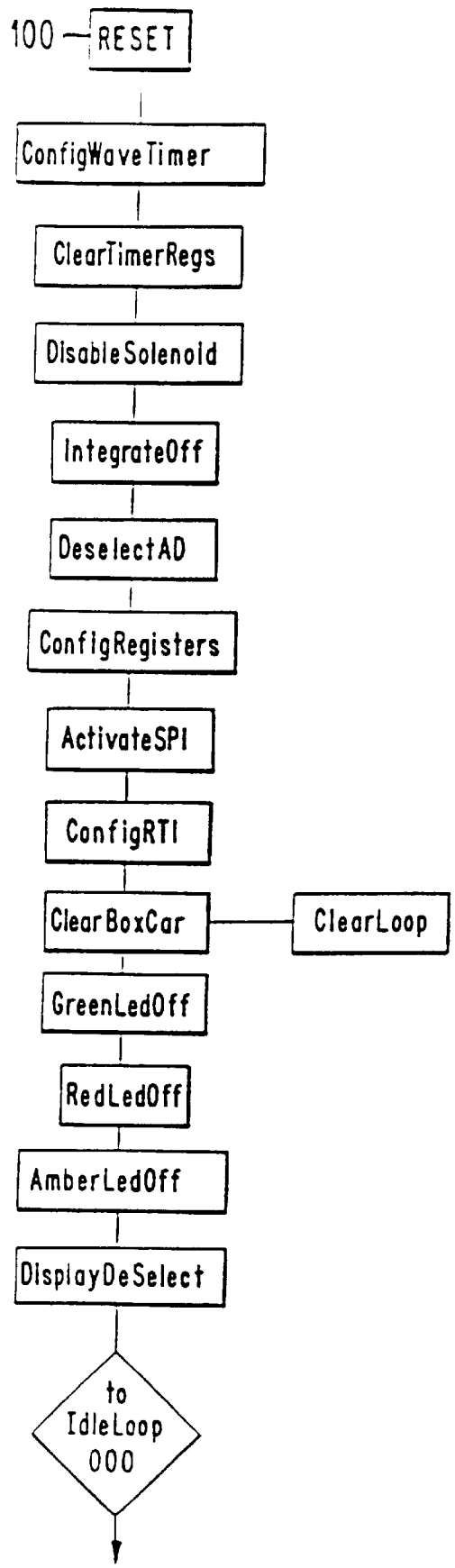
Figure 13B:
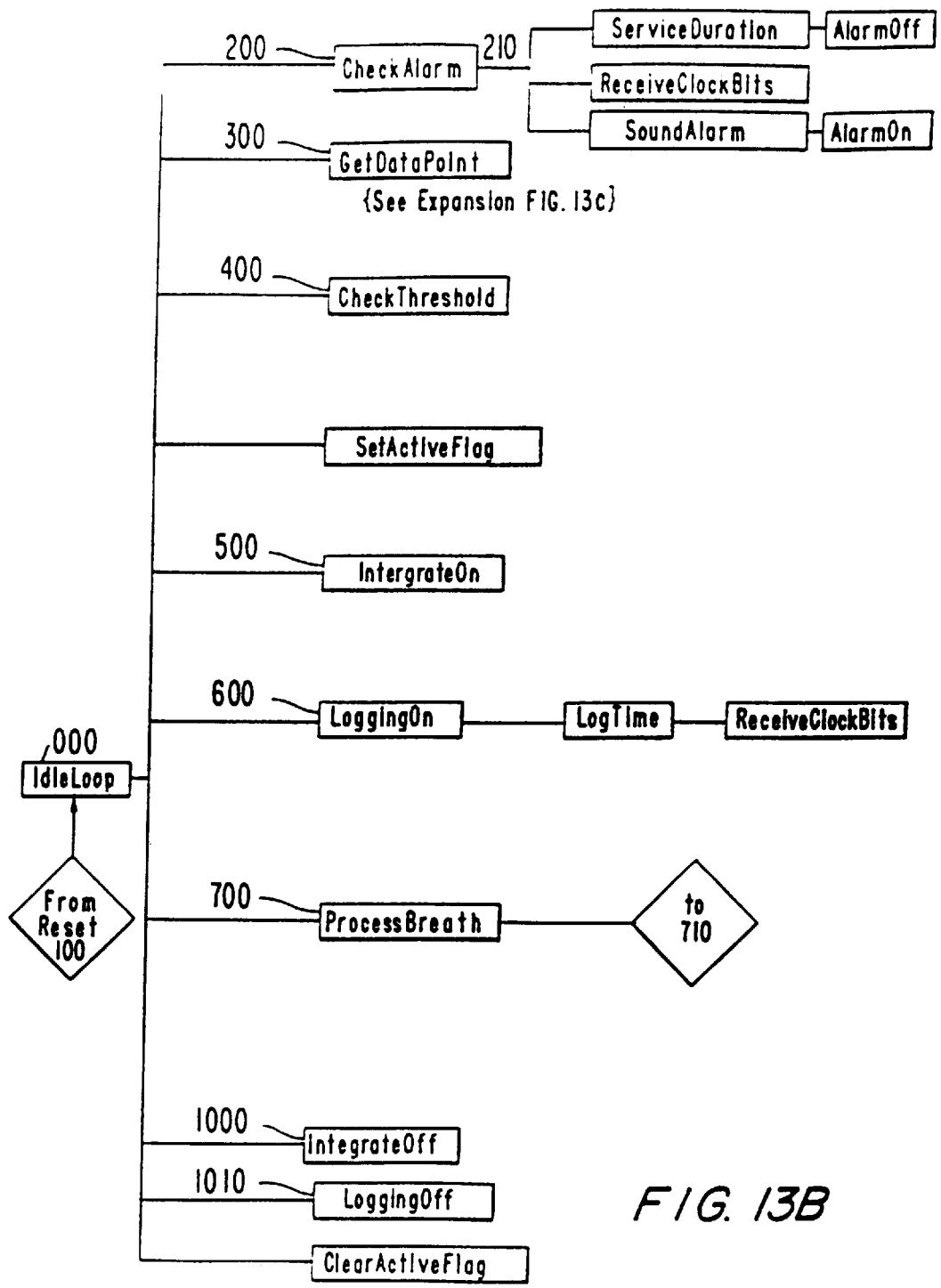
Figure 13C:
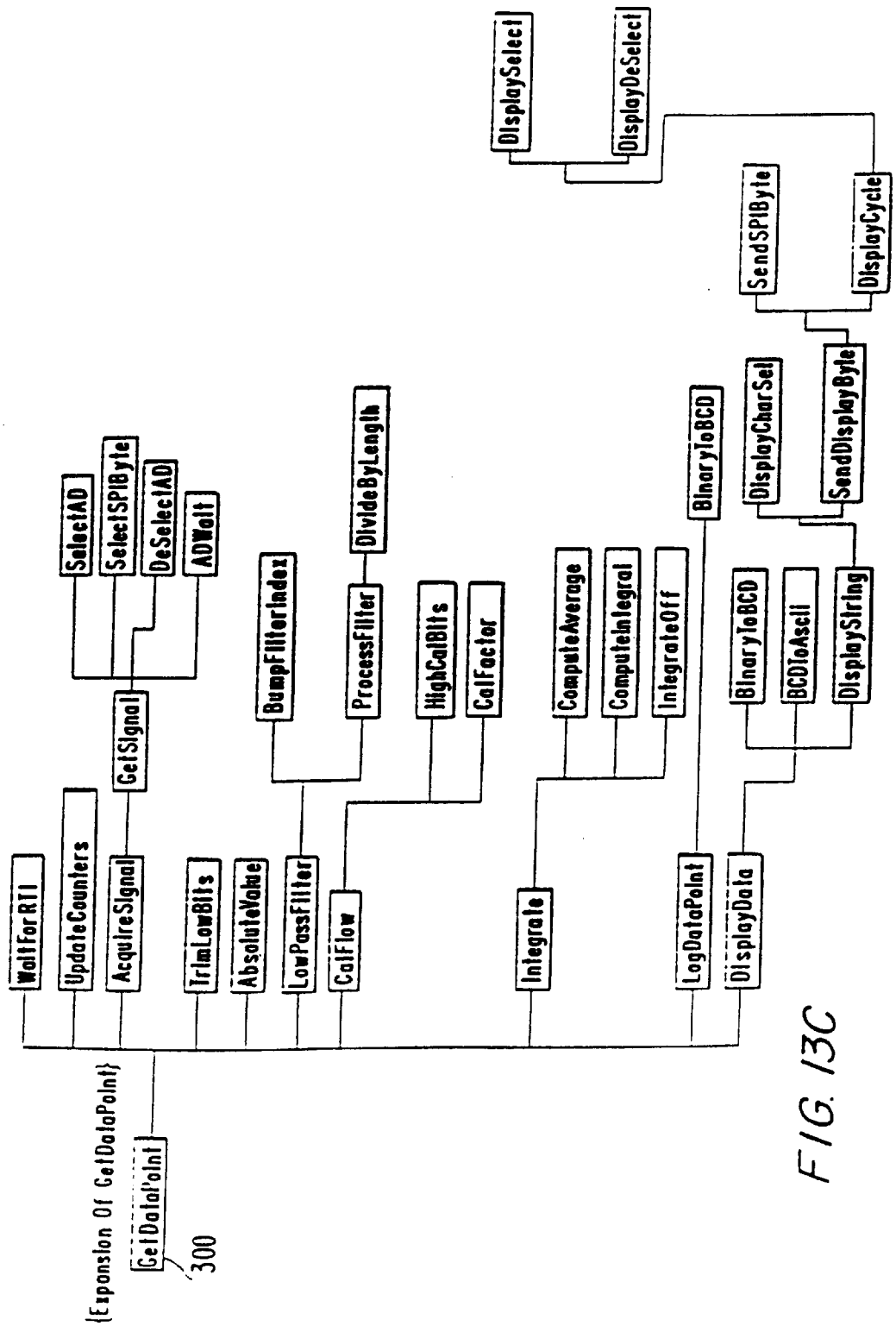

Referring to FIGS. 12 and 13C, flow is measured by the series of routines beginning with GetDataPoint. These routines perform data acquisition, signal processing, calibration, integration, data logging and information display functions.

Routine GetDataPoint begins by holding for a real time interrupt WaitForRTI, resulting in a 60 Hz sample rate because of initial configuration by the ConfigRTI routine executed during the Reset sequence. On a 1/60 second real time event mark, a flow data point is acquired from ADC 2210 by routine AcquireSignal.

The datapoint obtained from ADC 2210 by AcquireSignal is a 12 bit signed quantity (without sign extension). Signal processing begins by removing the lower two bits, which are assumed to be noise, by routine TrimLowBits, and proceeds with subsequent application of an 8 element moving average low pass digital filter by routine LowPassFilter.

The trimmed, low pass filtered flow data point value is then converted to its absolute value by routine AbsoluteValue and the sign bit stored for subsequent use by decision points requiring flow direction information (sign bit unity=>inhalation, sign bit zero=>exhalation).

The absolute value of the trimmed, filtered flow data point is then converted to a binary representation of flow in liters per minute by application of routine CalFlow. A rough conversion is first obtained by multiplying the uncalibrated value by two. A more accurate calibration is possible by applying correction factors to this rough calibrated value as a function of value. In the limit, one could store $2^n-1$ correction factors for an N bit value, thereby forming a calibration array for application to each digitized data point for overcoming arbitrary nonlinearity in the mapping of the differential pressure and the flow rate. In this embodiment, the array comprises 16 correction factors which are stored in a lookup table and applied to the rough calibrated value based on the value of the high four bits. Such an approach enables airway pneumotachs with non-linear pressure/flow characteristics to be employed. The details of the calibration algorithm are explained in the software appendix code listing under the section labeled Flow Calibration Data, although the calibration constants were set to zero in that embodiment for testing purposes.

The processed flow data point is then sent as argument to the integration routines Integrate. An integration algorithm described in detail in the code listing section labeled Integration Data is then performed.

The processed flow data point is then logged and the data display (showing the value of the shot counter, i.e., how many dosages of medication remain in canister 3200) is updated. If this flow is above the noise threshold, program control is transferred to branch point 500 and the breath processing functions, otherwise control returns to branch 200 and CheckAlarm and the alarm check functions are again executed.

Referring to FIGS. 12 and 13B, the breath processing functions begin at point 500 which starts the real time integration of measured airway flow to yield volume. Data logging is then begun at branch point 600 by storing the date, time and mode information in the data logging array in memory module 2100. The mode information is either ProgBreathMode at branch point 720 or CalBreathMode at branch point 730 as described below.

Subroutine ProcessBreath next begins at branch point 700 by further branching based on flow direction to the exhalation (peak flow meter function) or inhalation (drug delivery) routines.

Figure 13D:
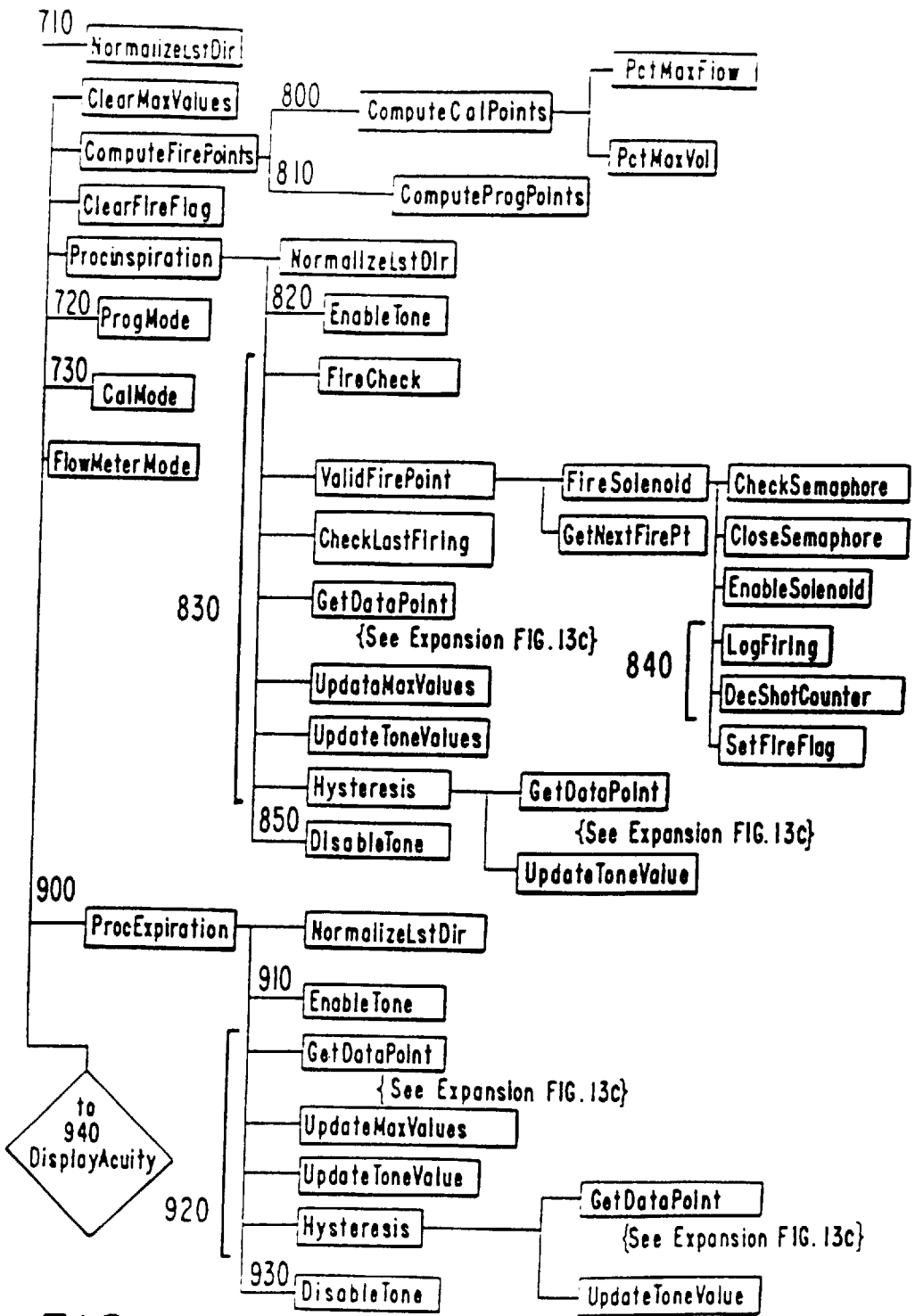
Figure 13E:
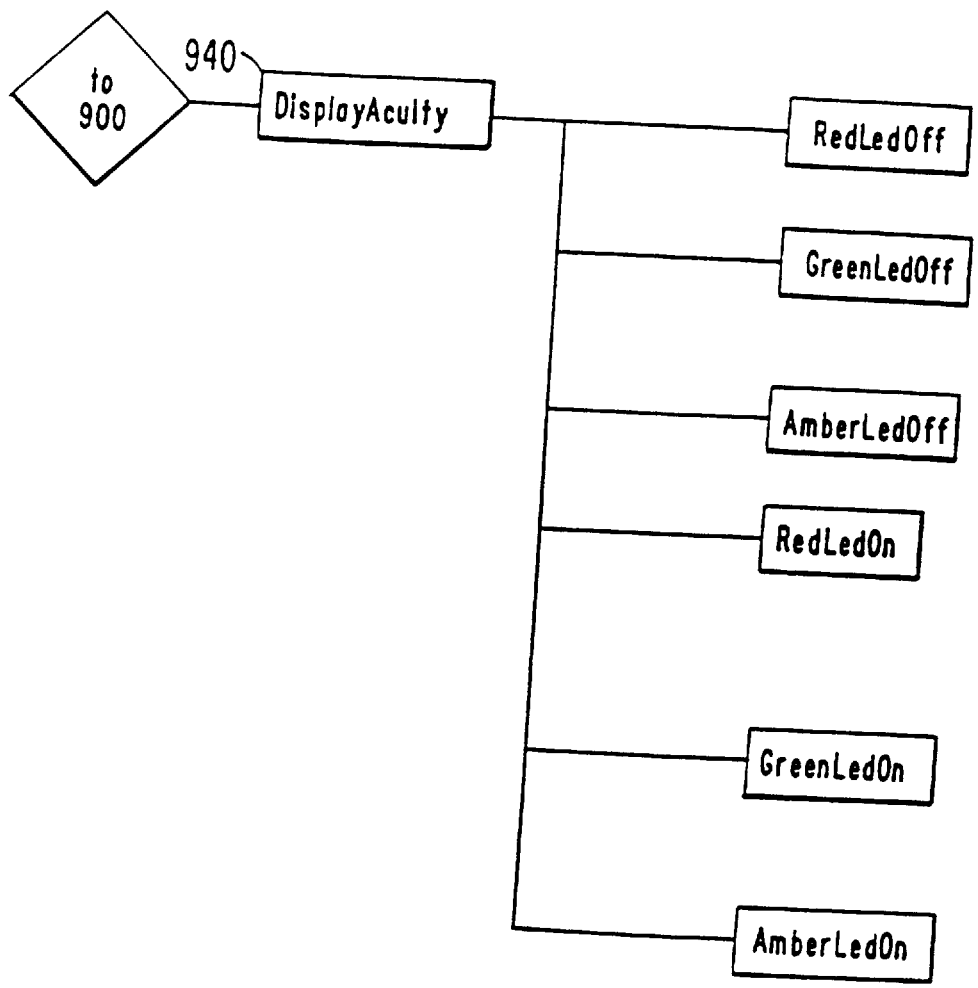

Referring to FIGS. 12 and 13D, the inhalation function begins at branch point 710 by checking for the current mode for drug delivery. If the device is in ProgBreathMode, or the device operates in the default mode (ProgBreathMode), the routine ProcessInspiration attempts to deliver drug at pre-programmed absolute flow and volume firing points. This process begins at branch point 810 where the flow and volume firing points pre-programmed in non-volatile system memory are copied into vectors FlowPoints and VolPoints. This process results in the production of "scheduled flow/volume firing points." An audible tone proportional to the instantaneous measured airway flow is started at point 820. Routines 830 continuously monitor the measured flow rate and volume during the inspiration and deliver drug as each successive pre-programmed flow/volume firing point now in vectors FlowPoints and VolPoints is reached. A flow/volume firing point is defined as a point during inspiration where both the instantaneous flow rate and flow volume are greater than or equal to a preprogrammed flow rate and flow volume pair.

Routines 830 then deliver drug as each firing point is reached. Routines 840 decrement the shot counter which provides a numeric character display for the user indicating the number of doses of drug remaining, and advance pointers stored at NxtFireFlow and NxtFireVol. These pointers will then be indicating the next flow/volume firing point (if preprogrammed) stored in vectors FlowPoints and VolPoints.

Flow/volume firing information for the Programmed Breath Mode is stored in the Firing Point Data area. The FireCount variable encodes the maximum number of possible firing points. Vectors FireFlow and FireVolume together encode flow/volume firing point pairs where FireFlow[i] and Firevolume[i] refer to firing point i. Flow rate is expressed in liters per minute, flow volume in liters. Preferably, as each firing point is reached, a uniform pulse is generated. In an alternate embodiment, variable size pulses may be generated in accordance with a selected schedule relating the time of delivery of the successive firing points to the desired location of deposition of the aerosol particles.

If the system is currently in CalBreathMode, i.e., calibration breath mode, control is transferred at branch point 710 to the routines ComputeCalPoints at branch point 800. These latter routines load the FlowPoints and VolPoints flow/volume firing point data arrays. Instead of copying preprogrammed flow/volume firing point data into the FlowPoints and VolPoints arrays as was done by routine ComputeProgPoints, routines at branch point 810, routines ComputeCalPoints at point 800 calculate flow/volume firing points based on the flow/volume maxima achieved during the preceding breath. This process results in the production of "scheduled flow/volume firing points."

Vectors PctFireFlow and PctFireVol contain the preprogrammed percent of maxima information used by routines ComputeCalPoints to make the flow/volume firing point calculations. These percent factors are encoded as the number of right shift operations needed to generate the desired percentage from a binary representation of the original value. Thus, unity represents 50%, two represents 25%, three represents 12.5% and so on.

Routines ComputeCalPoints apply percentage information contained in vectors PctFireFlow and PctMaxFlow to flow and volume maxima, respectively, measured during the last breath. A plurality of absolute flow/volume firing points (the exact number of firing points determined, as in ProgBreathMode, by the preprogrammed variable FireCount) are constructed, and placed in the FlowPoints and VolPoints vectors.

Control is then transferred to routines 820 and 830, and are again used, as they were in ProgBreathMode, to start an audible tone proportional to measured airway flow (routine EnableTone at branch point 820) and to deliver drug at the now appropriate flow/volume firing points (routines 830). The flow/volume firing points now resident in vectors FlowPoints and VolPoints are again consulted by routines 830 and used to trigger solenoid 3150 upon satisfaction of these thresholds.

It is the plurality of flow/volume firing point data loaded into the FlowPoints and VolPoints vectors by routines 800 and 810 respectively that distinguishes the behavior of the system during CalBreathMode and ProgBreathMode. In particular, during ProgBreathMode an attempt is made to deliver drug at invariant, pre-programmed firing points. During CalBreathMode, an attempt is made to deliver drug at flow/volume firing points determined through the application of pre-programmed percentage constants to the flow and volume maxima determined during the previous breath.

After all single inhalation scheduled drug deliveries have been made, or when measured flow changes direction, the audible tone proportional to flow is disabled by routine 850 and the appropriate mode for the next breath is determined at branch point 700. If some drug was delivered, it is assumed that the patient was making an acceptable inspiratory effort (even though all scheduled drug deliveries may not have taken place). In the case that some drug was delivered, the next mode will be ProgBreathMode, selected by routine ProgMode at branch point 720. On the other hand, if no drug was delivered, the assumption is made that the patient made an inadequate inspiratory effort, and was unable to meet any of the flow/volume firing point criteria for the previous breath. In this case, CalBreathMode is selected for the next breath by routine CalMode at branch point 730.

By entering CalBreathMode, the system is accommodating to individual patient characteristics when the patient has demonstrated an inability to generate sufficient inspiratory flow and volume to meet even one scheduled flow/volume firing point. By calculating new firing points as a fraction of flow/volume parameters actually achieved during the previous breath, the chance of achieving a drug delivery during the subsequent breath becomes more likely. In other words, if none of the more desirable (i.e., relatively late in the cycle) scheduled flow/volume firing points can be met by a patient's inspiratory effort, then new scheduled flow/volume firing points occurring earlier in the inspiratory cycle, i.e., at relatively lower flow rates and flow volumes, are more desirable than no drug delivery at all.

In accordance with the present invention, if no drug is delivered during an inspiration in the CalBreathMode, CalBreathMode will again be entered, and new scheduled flow/volume points corresponding to lower flow rates and volumes will be calculated based on the new flow/volume maxima achieved during the most recent previous breath. This strategy virtually ensures that some drug will be eventually delivered, even if the patient's inspiratory effort is deteriorating from breath to breath.

Referring to FIGS. 12, 13B, and 13D, after selection of the next breath mode by routines ProgMode at point 720 or CalMode at point 730, the integration process is stopped by routine IntegrateOff at point 1000 and the data logging stopped by routine LoggingOff at point 1010. During each breath, a log of all measured flow data is kept in an array into which is also stored the time and date, mode and (flow) points in the array where drug was delivered. The format of this array can be found in the software appendix code listing in the section labeled Data Logging Area.

This completes the description of the behavior of the software branching routines during an inhalation.

Referring to FIGS. 12, 13B, and 13D, if an exhalation is detected at decision branching point 700, control is transferred to exhalation handling routines ProcExpiration at branching point 900. Routine EnableTone at point 910 activates an audible tone proportional to measured airway flow. Flow is continuously measured and data points are logged until flow direction reverses. Routines 920 detect peak flow by noting the flow prior to the point of flow reversal. This peak flow point is mapped into a three level clinical acuity index by routines DisplayAcuity at point 940 through the use of pre-programmed constants stored at AcuityGreen, AcuityAmber and AcuityRed. The appropriate declarations can be found in the software appendix code listing in the section labeled Pulmonary Function DATA.

If the measured peak flow is greater than or equal to the value stored at AcuityGreen, a green light emitting diode is illuminated by routines 940 indicating that the patient's condition is nominal. If the measured peak flow is greater than or equal to the value stored at AcuityAmber, and less than the value stored at AcuityGreen, an amber light emitting diode is illuminated by routines 940 indicating that the patient's condition is marginal. If the measured peak flow is greater than or equal to the value stored at AcuityRed, and less than the value stored at AcuityAmber, a red light emitting diode is illuminated by routines 940 indicating that the patient's condition is unacceptable.

Subsequent to display of the acuity index, the integration is stopped by routine IntegrateOff at point 1000. Note that volume information is not used during the processing of an exhalation by this embodiment. However, in an alternate embodiment, such volume data could be used to calculate valuable pulmonary function indices such as the FEV1 (volume exhaled in one second) and vital capacity (VC). The FEV1 could be used to provide more clinical acuity information to the patient than the three level index based on peak expiratory flow now displayed. Further note that, although the volume information is not being used to calculate the FEV1 in this embodiment, the FEV1 could be calculated later through analysis of the logged flow points of data.

Control then continues to routine LoggingOff at point 1010 which stops data logging, as was done during inhalation mode described earlier.

The preferred embodiment makes extensive use of internally programmed constants which influence the system behavior. These constants are readily changed in the current embodiment through the use of a microprocessor emulator system which allows an MS-DOS computer to be used to arbitrarily modify a plurality of non-volatile system memory locations containing either program or data.

It is intended that the software programs be flexible in design so that the system can be configured for use with a particular patient by selecting certain processing subroutines, calibration coefficients, and operating parameters from a library of such information, or from an external source, for use by the main program to accommodate patient specific or drug specific requirements in different applications to treat predetermined medical conditions. Thus, the software controlling the device can be configured or customized for a specific use by a specific patient. Accordingly, when the device is used for a different patient or medication or both, the software can be reconfigured for such use.

In another alternate embodiment of the present invention, the software is programmed to measure pulmonary function periodically, preferably prior to each administration of a dosage, and look for changes in the detected flow patterns and measured pulmonary functions of the patient during the course of treatment. Those detected changes are then used to modify the treatment parameters in accordance with the improved or degenerated condition of the patient. For example, the dosage per administration and the frequency of administration could be adjusted as indicated by detected changes in the patient's condition. Similarly the dosage could be adjusted from administration to administration by measuring the time between administration to determine a maximum allowed dosage based on accepted medical practices.

In another alternate embodiment of the present invention, each canister 3200 is provided with a code that identifies the contents of the canister, and system electronics 3400 includes means (not shown) for reading a code associated with canister 3200. In one such embodiment, the code is entered externally and in another such embodiment the code is provided automatically when canister 3200 is inserted into base 3100. The code may be read each time canister 3200 is inserted into base 3100 and used by microprocessor 2000 to customize the software programming for delivery of the particular medication. In one embodiment, the code is in the form of product labeling, e.g., a universal bar code, and a code sensor for reading a printed universal bar code (not shown) comprises a photodetector array and a light emitting diode to provide illumination for the photodetector array to read the bar code. Preferably, the bar code is of the circular form so that it can be read regardless of the orientation of canister 3200 in base 3100. In another embodiment, the code may be a digital word integral with the canister and a code sensor for reading the digital word could include electrodes in the base for engaging the code that are connected to the microprocessor. If necessary, the changes in the software for delivery of a particular drug that cannot be provided by a code scheme could be installed in microprocessor 2000 software at the time the device and medication are given to the patient. Alternately, the microprocessor could be configured to request the information from an external source when the code provided is not in the library of selected medications. This programming may be performed by changing the EEPROM or its contents by providing appropriate instructions to microprocessor 2000 or its associated memory through a conventional external communications port.

Preferably, the code also identifies the application for that medication in circumstances where the medication is useful for more than one application or may be used in conjunction with more than one carrier composition having different affinities for deposition. Thus, the code will provide information concerning dosage amounts and times and will provide the information for controlling solenoid 3150 to select an aerosol having a desired particle size distribution for favorable deposition into desired locations in the patient's pulmonary system. This will ensure that the medication is delivered in accordance with its intended delivery characteristics and protocols.

In an alternate embodiment, the software routine could be modified to operate in the calibrated breath mode all the time such that a first breath flow must be acquired and evaluated to identify initial desired threshold firing point or points in the measured flow to administer the medication for the most efficacious inspiration, and to use that information during a second inspiratory flow to actuate solenoid valve 3150 to administer the medication when the flow in a second acquired inspiration corresponds to the identified threshold desired points. In this embodiment, speaker module 2700 could be driven by microprocessor 2000 to prompt the patient to conduct the second inspiration with the same breathing pattern used in the first measured inspiration by recording the flow rate tones of the first inspiration and regenerating those tones in the second breath.

Measuring flow without drug delivery also provides several advantages. For example, displaying the visual acuity index corresponding to the measured expiratory flow can instruct the patient to seek immediate medical attention. Thus, the patient is advised of the need for medical attention when they might not otherwise realize that they need it. This is of particular concern when a patient has just been to a doctor and, absent such displayed information, would not think it necessary to return to the doctor so soon, waiting instead for the prescribed medication to take effect. For another example, it permits obtaining an initial or baseline breath pattern for the patient based on one or more inspirations and expirations e.g., FEV1, vital capacity, and peak expiratory flow. If more than one breath pattern is used to obtain the baseline, the recorded data can be averaged to form the baseline pattern. This baseline can be used to determine gross changes in the patient's pulmonary functions which can be displayed to the patient or relayed to the medical examiner or both to provide an ongoing assessment of the therapy program.

Obtaining a baseline pattern provides several advantages. First, the determined pattern can be used to determine the optimum point or points in the inspiratory flow for delivery of aerosolized medication for the selected medication in its particular application. Thus, the administration of the drug can be based on the patient's actual flow patterns, including inspiratory flow, inspiratory pause, and expiratory flow, and automatically released when the predetermined point or points in the flow occurs. This permits adapting the device to the patient and providing a more effective means for delivering aerosolized medication.

Second, the patient's determined baseline flow pattern can be used as a predictor to account for changes in the patient's breath patterns. Thus, a subsequent inspiration, during which the aerosolized medication will be delivered, can be detected in real time and compared to the previously determined baseline pattern. Any differences in the patterns can be identified. The baseline pattern can then be used to predict the remaining portion of the real time inspiratory flow taking into account the prior deviations in the real time inspiration. This permits adjusting in real time the actual point or points to administer medication, as compared to basing the administration on the occurrence of the predetermined optimal point or points derived from the baseline pattern. Thus, breath to breath variations in the patient's breathing patterns can be identified and used to adjust the administration of medication.

Third, the determined pattern can be used to generate an audible prompt, for example, a tone generated by speaker 2740 that changes in volume or frequency to correspond to changes in the predetermined baseline breath pattern. Thus, the tone can be used to prompt the patient to follow the previously determined baseline breathing pattern so that the delivery of aerosolized medication can be predictably delivered at the desired point or points in the patient's breathing pattern. The prompt, based on the predetermined breathing pattern, thus helps improve the efficiency of the drug delivery.

Fourth, the determined baseline pattern can be compared to a preferred ideal breathing pattern for optimal delivery of the medication. If substantial differences are found to exist, which differences might affect the efficacy of the drug, the prompt then could be used to drive the patient's breathing pattern, i.e., to prompt the patient to modify his or her regular "baseline" breathing pattern to conform more or less to the ideal desired pattern for that medication. Thus, the prompt can improve the efficiency of the drug delivery.

In addition, by recording a series of actual inspiratory and expiratory flow data taken over extended time periods, with or without the contemporaneous administration of medication, trend data can be obtained for analyzing the relative success of the drug therapy. This can then be used by microprocessor 2000 in accordance with its software instructions to alter the drug therapy, for example, the dosage of the medication delivered with each administration or the frequency of administration or both. Also, the trend data can be used by the medical examiner to provide additional data regarding the drug therapy to study the drug therapy originally prescribed and to alter the drug therapy as necessary.

Microprocessor 2000 also may be programmed to review the history of the last several administrations of medication prior to an indicated administration to prevent a patient from administering an overdose of medication or to indicate to the patient that insufficient amounts of medication have been administered.

In an alternate embodiment, each canister 3200 may be provided with a battery supply (not shown) and appropriate electrodes to interface with a corresponding receptacle with electrodes on base 3100 (not shown) for powering some portion or all of electronics 3400 of the device. In one embodiment, the battery supply has an expected lifetime that will be sufficient to actuate whatever electromechanical valve is used to administer all of the contents of the canister, and, where appropriate, perform the anticipated flow measurements taken with or without administration of medication, for a given course of therapy involving that particular medication. This advantageously provides for an adequate power supply for operation of the device with a particular medication without requiring the patient to obtain a supply of batteries for use and without regard to what medication is to be administered. In another embodiment, the canister battery is used for example, to power the electromechanical device used to actuate the valve to release aerosol medication, but not to power the flow measuring electronics, the latter being powered by a separate battery located in base 3100 (not shown).

It has been discovered, using the method of cascade impingement to determine an aerodynamic diameter, that by delivering the aerosolized medication in a series of pulses, as contrasted with a single metered dose, the respirable fraction of the delivered aerosolized compound is substantially increased. More particularly, it has been discovered that the aerosol particle size distribution in a pulse sequence is related to the duration of the pulse within the sequence and can be changed by adjusting the duty cycle of the pulses used to generate the aerosol. This effect may be due to more rapid evaporation of propellant or carrier during a short duty cycle pulse sequence as compared with a single pulse.

In one example, a conventional metered dose inhaler device was compared to a device of the present invention using the method of cascade impingement. It was empirically determined that the metered dose inhaler produced a respirable fraction of about 36%. In contrast, the device in accordance with the present invention, operating to deliver the same dose (by weight) in a pulsatile fashion having four uniform discrete pulses, each pulse having a duty cycle of 13% having a pulse width of 112 msec, corresponding to an on time of 14.56 msec and an off time of 97.44 msec, provided a respirable fraction of about 41%. This is believed to be a substantial improvement in aerosol drug delivery.

The method of cascade impingement can be used in an iterative manner to determine empirically the pulse parameters for maximizing the respirable fraction of the aerosolized compound to be delivered. It should be understood, however, that the term "maximized respirable fraction" refers to a selected respirable fraction that is substantially improved as compared to the respirable fraction produced by a standard metered dose inhaler device, but is not intended to refer to an absolute maximum respirable fraction relative to that produced by a metered dose inhaler device.

In accordance with the present invention, valve 3150 is controlled by microprocessor 2000 and is used as a high frequency switch to release a series of pulses of the aerosol medication having a selectable width, shape, and frequency. The pulses are delivered to the patient through nozzle 3160 mouth end 3142 mouthpiece 3110. By selecting the time period and frequency that valve 3150 is open, the pulse width and interval between adjacent pulses can be selected. Having selected for the desired particle size, the patient's breathing pattern can then be used to identify the optimal points or points at which to deliver the pulses of aerosol medication for delivery to the desired locus or loci in the airway. Further, the selected particle size can then be used with an optimal inspiratory flow, inspiratory pause, expiratory flow, and tidal volume to deliver the aerosol medication to the most therapeutically efficacious locations in the patient's airway. It should be understood that each such dose given as a sequence of pulses can be deposited at different loci by changing the delivery schedule with respect to at which point or points in the inspiratory flow the aerosol is delivered for inspiration.

Valve 3150 also can be used to control the total dosage delivered during a single administration by providing a selected number of pulses of equal width, or a first selected number of pulses of a first width and a second selected number of pulses of a second width, whether those first and second pulses are delivered in succession, alternately, or randomly, synchronously or asynchronously. Further, valve 3150 could be used to administer the desired dosage over more than one inspiration in the event that the drug therapy requires a dosage that could not be practicably administered in a single inspiration. Changes in the location or the total dosage can be made through changing the control information provided to solenoid valve 3150 by microprocessor 2000 to produce the desired number and size of pulses in response to the desired delivery schedule.

In accordance with this alternate embodiment of the invention, another function of microprocessor 2000 is to select an optimum particle size and delivery schedule for the medication to be administered for the patient. This is achieved by evaluating the specific medication to be delivered, and the nature of the condition, e.g., whether the drug is to be delivered to the large airways, small airways, or both. This function may be enhanced by also evaluating measured flow and determining optimum points in the measured flow to administer the medication, and using that information in a successive inspiratory flow to administer the medication at an appropriate time as discussed herein.

In accordance with an alternate embodiment, the canisters containing the medication could be constructed with an electromechanical valve actuator integral to the canister. Preferably, the actuators are powered by a battery supplied with the canister. In such an embodiment (not shown) the microprocessor would interface with the canister to provide control signals to actuate the valve actuator to select the desired pulse width, interval, and frequency as appropriate for the given circumstances.

In accordance with another embodiment, the apparatus may be provided with a motion detector for determining when the canister of aerosol generating material has been adequately agitated. In this embodiment, the motion detector can be used to prevent delivery of any aerosol until the device indicates that the material has been agitated to cause the material to be sufficiently mixed to provide the desired aerosol. This device is believed to overcome the problem of segregation or sedimentation of the medication and any aerosol precursor, propellant, or carrier material, which is common to canisters containing medication to be delivered in an aerosol, including metered dose devices. Examples of suitable motion detectors include mercury switches that generate a signal in response to the degree of agitation, which signal is then processed to determine when a sufficient amount of agitation has occurred, whereupon the device is then enabled for delivery of an amount of aerosol.

It also should be understood that other valve switch means for releasing pulses of aerosol could be used in place of an integral solenoid and valve. For example, a solenoid could be used to depress the valve stem of a simple canister valve or to move the canister relative to the valve stem, thereby to provide the appropriate pulses.

One preferred application for the present invention is for bronchodilator therapy for asthma. In this embodiment, the device can be used to select for the proper particle size and dosage by providing a plurality of pulses having different or nonuniform widths at different points in the inspiratory cycle to provide small particles for deposition in the small airways and large particles for deposition in the large airways in sufficient amounts to treat effectively the condition. Measured improvements in pulmonary function can then be used to reduce the dosage both in terms of number of pulses and frequency of administrations.

In another application, the device could be used for treatment of a bronchial constriction in the small airways by providing high frequency pulses during optimal points in the inspiratory flow to produce small particles that deposit in the small airways. Measured improvements in pulmonary function can then be used to reduce the dosage both in terms of number of pulses in a given administration and in the frequency of administrations.

Other anticipated uses of the present invention could be to provide optimal delivery of drugs in aerosol form, based on measured inspiratory and expiratory flow, such as beta-agonists, e.g., albuterol for bronchial-constriction, inhaled steroids for bronchial inflammation, pentamidine for pneumocystis prophylaxis in patients who have tested positive for HIV, narcotics, e.g., morphine or other opiate derivatives, for patients having chronic pain, allowing for effective self-medication exploiting the rapid onset of an aerosol medication administration technique, and without substantial risk of overdosing, and with providing the medical examiner a record of the drug administration for evaluation in the event of continued therapy. See also, e.g., the medications identified in D. Kohler, *Lung* (1990) supp., p. 679. The terms inspiration and inhalation are used interchangeably herein and the terms expiration and exhalation are used interchangeably herein. It also should be understood that in place of a software driven microprocessor the present invention could be implemented using a finite state machine, including without limitation solid state finite state machines.

It also should be understood that the terms aerosol and aerosol generating material are used, in the context of this invention, generally to include the medicinal compound and any carrier or propellant, whether a liquid, gas, or solid material.

One skilled in the art will appreciate that the present invention can be practiced by other than the described embodiments, which are presented for purposes of illustration and not of limitation, and the present invention is limited only by the claims.

We claim:

1. A drug delivery canister, comprising:
    a cylindrical container having a valved opening therein which valve prevents release of container contents until actuated;
    a pressurized formulation of a pharmaceutically active drug and pharmaceutically acceptable carrier in the container; and
    a resistor having a set resistance value wherein the resistor identifies the pharmaceutically active drug.

2. The canister of claim 1 wherein the resistor identifies a method of administration of the formulation in the canister.

3. The canister of claim 2, wherein the method of administration comprises release of the formulation from the canister in an aerosol with desired particle size distribution for favorable deposition into desired locations in a patient's pulmonary system.

4. The canister of claim 1, wherein the resistor identifies a method of release of formulation from the canister so as to obtain a desired delivery characteristic.

5. The canister of claim 1, further comprising:
    a battery supply unit and electrodes for corresponding with electrodes on a device to which power is to be supplied.

6. A hand held device for delivering an aerosolized medication to a patient for inspiration, comprising:
    a tube forming a flow path from an open end to a mouth end;
    a canister comprising
        a cylindrical container having a valved opening therein which valve prevents release of container contents until actuated;
        a pressurized formulation of a pharmaceutically active drug and pharmaceutically acceptable carrier in the container;
        a resistor having a set resistance value wherein the resistor identifies the pharmaceutically active drug;
    a nozzle for releasing and aerosolizing medication from the canister to the open end of the tube;
    a flow transducer for measuring the patient's breath flow through the tube;
    a microprocessor for calculating a medication delivery point based on information from the flow transducer; and
    an actuating mechanism which initiates release of medication through the nozzle and into the tube upon receipt of a signal sent after the microprocessor has determined that the patient's breath flow is at the delivery point.

7. The device of claim 6 wherein the delivery point is calculated to maximize the efficacy of the medication.

8. The device of claim 7, further comprising:
    a means for detecting breath parameters of the patient including inspiratory flow and expiratory flow.

9. The device of claim 8, further comprising:
    a visual indicator providing a visual display of detected breath parameters.

10. The device of claim 6, wherein the microprocessor includes a library of administration protocols for different medications.

11. The device of claim 6, further comprising:
    a battery supply and electrodes electrically connected thereto.

* * * * *